(12) United States Patent
Lan et al.

(10) Patent No.: US 9,580,443 B2
(45) Date of Patent: Feb. 28, 2017

(54) HETEROCYCLIC DERIVATIVES AS MODULATORS OF KINASE ACTIVITY

(71) Applicant: Merck Patent GmbH, Darmstadt (DE)

(72) Inventors: Ruoxi Lan, Waltham, MA (US); Bayard R. Huck, Sudbury, MA (US); Xiaoling Chen, Chestnut Hill, MA (US); Yufang Xiao, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/432,316

(22) PCT Filed: Nov. 15, 2013

(86) PCT No.: PCT/US2013/070261
§ 371 (c)(1),
(2) Date: Mar. 30, 2015

(87) PCT Pub. No.: WO2014/078637
PCT Pub. Date: May 22, 2014

(65) Prior Publication Data
US 2015/0274750 A1    Oct. 1, 2015

Related U.S. Application Data

(60) Provisional application No. 61/727,298, filed on Nov. 16, 2012.

(51) Int. Cl.
| | | |
|---|---|---|
| A61K 31/535 | (2006.01) | |
| A01N 43/58 | (2006.01) | |
| A01N 43/60 | (2006.01) | |
| A61K 31/50 | (2006.01) | |
| A61K 31/495 | (2006.01) | |
| A01N 43/90 | (2006.01) | |
| A61K 31/519 | (2006.01) | |
| C07D 265/36 | (2006.01) | |
| C07D 498/02 | (2006.01) | |
| C07D 265/30 | (2006.01) | |
| C07D 295/00 | (2006.01) | |
| C07D 471/00 | (2006.01) | |
| C07D 487/00 | (2006.01) | |
| C07D 498/04 | (2006.01) | |
| C07D 487/04 | (2006.01) | |
| A61K 31/496 | (2006.01) | |
| A61K 31/517 | (2006.01) | |
| A61K 31/5383 | (2006.01) | |
| A61K 45/06 | (2006.01) | |
| A61N 5/10 | (2006.01) | |
| C07D 239/70 | (2006.01) | |
| C07D 471/04 | (2006.01) | |

(52) U.S. Cl.
CPC ......... *C07D 498/04* (2013.01); *A61K 31/496* (2013.01); *A61K 31/517* (2013.01); *A61K 31/519* (2013.01); *A61K 31/5383* (2013.01); *A61K 45/06* (2013.01); *A61N 5/10* (2013.01); *C07D 239/70* (2013.01); *C07D 471/04* (2013.01); *C07D 487/04* (2013.01); *A61N 2005/1098* (2013.01)

(58) Field of Classification Search
None
See application file for complete search history.

(56) References Cited

FOREIGN PATENT DOCUMENTS

| WO | 03064397 A1 | 8/2003 |
|---|---|---|
| WO | 2004/092154 A1 | 10/2004 |
| WO | 2005/033086 A1 | 4/2005 |
| WO | 2005/039506 A2 | 5/2005 |
| WO | 2005/054237 A1 | 6/2005 |
| WO | 2005/056014 A1 | 6/2005 |
| WO | 2005/117909 A2 | 12/2005 |
| WO | 2006/071819 A1 | 7/2006 |
| WO | 2006/120573 A2 | 11/2006 |
| WO | 2006/131835 A2 | 12/2006 |
| WO | 2006/136821 A1 | 12/2006 |

(Continued)

OTHER PUBLICATIONS

Barlund et al., Multiple Genes at 17q23 Undergo Amplification and Overexpression in Breast Cancer, Cancer Res., 2000, 60:5340-5344.
Bundgaard H. ed., Design and Application of Prodrugs, 1985, Harwood Academic Publishers Gmfh.
Burger's Medicinal Chemistry and Drug Discovery 6th ed. (Donald J. Abraham ed., 2001, Wiley).
Couch et al., Localization of PS6K to Chromosomal Region 17q23 and Determination of Its Amplification in Breast Cancer, Cancer Res., 1999, 59:1408-11.
Foster A., Deuterium Isotope Effects in the Metabolism of Drugs and Xenobiotics: Implications for Drug Design, Advances in Drug Research, 1985, 14: 1-39.
Garcia-Bustos J. et al., PIK1, an essential phosphatidylinositol 4-kinase associated with the yeast nucleus, EMBO J., 1994, 13(10):2352-2361.

(Continued)

*Primary Examiner* — Jeffrey H Murray
(74) *Attorney, Agent, or Firm* — Dwight D. Kim; EMD Serono Research and Development Institute

(57) ABSTRACT

The invention provides novel imidazol-piperidinyl derivatives of the formula (I)

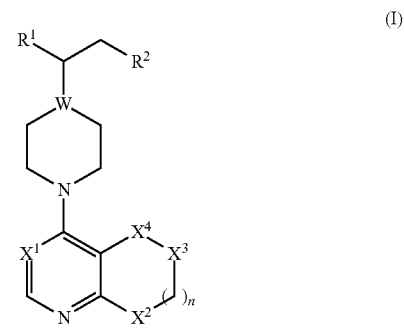

in which $R^1$, $R^2$, W, $X^1$, $X^2$, $X^3$, $X^4$ and n have the meanings indicated in formula I, and their manufacture and use for the treatment of hyperproliferative diseases, such as cancer.

14 Claims, No Drawings

(56) References Cited

FOREIGN PATENT DOCUMENTS

| WO | 2007/072017 A2 | 6/2007 |
| WO | 2008/075109 A1 | 6/2008 |
| WO | 2008/140947 A1 | 11/2008 |
| WO | 2010/056563 A1 | 5/2010 |
| WO | 2010/093419 A1 | 8/2010 |
| WO | 2012/013282 A1 | 2/2012 |
| WO | 2012/016001 A1 | 2/2012 |
| WO | 2012/069146 A1 | 5/2012 |
| WO | 2013/040044 A1 | 3/2013 |

OTHER PUBLICATIONS

Gillette et al., Theory for the Observed Isotope Effects on the Formation of Multiple Products by Different Kinetic Mechanisms of Cytochrome P450 Enzymes, Biochemistry, 1994, 33: 2927-2937.

Hanks, S.K. and Hunter T., The eukaryotic protein kinase superfamily: Kinase (catalytic) domain structure and classification, FASEB J., 1995, 9:576-596.

Hanzlik et al., Active Site Dynamics of Toluene Hydroxylation by Cytochrome P-450, J. Org. Chem., 1990, 55: 3992-3997.

Hardie and Hanks, The Protein Kinase Facts Book. I and II, 1995, Academic Press, San Diego, CA.

Hiles et al., Phosphatidylinositol 3-Kinase: Structure and Expression of the 110 kd Catalytic Subunit, Cell, 1992, 70:419-429.

Jarman et al., The deuterium isotope effect for the a-hydroxylation of tamoxifen by rat liver microsomes accounts for the reduced genotoxicity of [D5-ethyl}tamoxifen, Carcinogenesis, 1995, 16(4): 683-688.

Knighton et al., Crystal Structure of the Catalytic Subunit of Cyclic Adenosine Monophosphate-Dependent Protein Kinase, Science, 1991, 253:407-414.

Kunz et al., Target of Rapamycin in Yeast, TOR2, Is an Essential Phosphatidylinositol Kinase Homolog Required for G1 Progression, Cell, 1993, 73:585-596.

Reider et al., Synthesis of (R)-Serine-2-d and Its Conversion to the Broad Spectrum Antibiotic Fludalanine, J. Org. Chem., 1987, 52: 3326-3334.

Wu et al., 17q23 Amplifications in Breast Cancer Involve the PAT1, RAD51C, PS6K, and SIGMA1B Genes, Cancer Research, 2000, 60: 5371-5375.

HETEROCYCLIC DERIVATIVES AS MODULATORS OF KINASE ACTIVITY

RELATED APPLICATION

This application is a U.S. national stage application of international application PCT/US2013/70261, filed on Nov. 15, 2013, which claims the benefit of U.S. Ser. No. 61/727,298, filed on Nov. 16, 2012. The contents of the aforementioned applications are incorporated herein in their entireties by reference.

FIELD OF THE INVENTION

The invention relates to a series of heterocyclic compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

BACKGROUND

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375). The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumor suppressor LKB1 activates AMPK which phosphorylates the TSC1/2 complex and enables it to inactivate the mTOR/p70S6K pathway.

Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. P70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/056563, WO 10/093419, WO 12/013282, WO 12/016001 and WO 12/069146.

SUMMARY OF THE INVENTION

The invention provides for compounds of formula I which are useful to treat p70S6K related disorders.

DESCRIPTION OF THE INVENTION

It is the object of the present invention to provide novel compounds that modulate kinase activity. This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel heterocyclic derivatives and pharmaceutically acceptable salts, solvates, solvates of salts, tautomers or stereoisomers, including mixtures thereof in all ratios thereof, that are kinase inhibitors and useful in the treatment of the above mentioned diseases.

The invention relates to compounds of the formula (I)

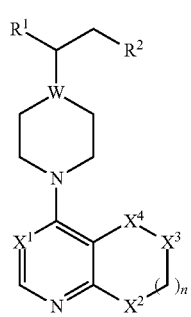

(I)

and pharmaceutically acceptable salts, solvates, solvates of salts, tautomers or stereoisomers, including mixtures thereof in all ratios thereof,
wherein:
$X^1$ is N or CH,
$X^2$ is $CH_2$ or NH,
$X^3$ is $CH_2$ or CO,
$X^4$ is O, $CH_2$ or NH,
W is N or CH,
$R^1$ is Ar or Het,
$R^2$ is $[C(R^3)_2]_p Het^1$ or $[C(R^3)_2]_p N(R^3)_2$,
$R^3$ is H or alkyl with 1, 2, 3, or 4 C-atoms, which is optionally substituted;
Ar is phenyl which is unsubstituted or mono-, di- or trisubstituted by Hal, A, phenyl, $CON(R^3)_2$, $COOR^3$, NHCOA, $NHSO_2A$, CHO, COA, $SO_2N(R^3)_2$, $SO_2A$, $[C(R^3)_2]_p OR^3$, $[C(R^3)_2]_p N(R^3)_2$ and/or $[C(R^3)_2]_p CN$,
Het is furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, pyrazinyl, indolyl, isoindolyl, benzimidazolyl, indazolyl or quinolyl, which is unsubstituted or mono-, di- or trisubstituted by Hal, A, $[C(R^3)_2]_p OR^3$, $[C(R^3)_2]_p-N(R^3)_2$, $NO_2$, ON, $[C(R^3)_2]_p COOR^3$, $CON(R^3)_2$, $NR^3 COA$, $NR^3 SO_2 A$, $SO_2 N(R^3)_2$, $S(O)_m A$ and/or $O[C(R^3)_2]_q N(R^3)_2$,
$Het^1$ is dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, azepanyl, morpholinyl, hexahydropyridazinyl, hexahydropyrimidinyl, [1,3]dioxolanyl, tetrahydropyranyl, pyridyl or piperazinyl, which is unsubstituted or mono- or disubstituted by A,
A is unbranched or branched alkyl with 1-10 C-atoms, wherein one or two non-adjacent CH- and/or $CH_2$-groups may be replaced by N-, O- and/or S-atoms and wherein 1-7H-atoms may be replaced by F or Cl,
Hal is F, Cl, Br or I,
each m is independently 0, 1 or 2,
each n is independently 0, 1 or 2,
each p is independently 0, 1, 2, 3 or 4,
each q is independently 2, 3 or 4.

The invention also relates to the optically active forms (stereoisomers), the enantiomers, the racemates, the diastereomers and the hydrates and solvates of these compounds.

The invention also relates to the solvates of the salts of the compounds of formula I, e.g. the mono- or dihydrate of the hydrochloride.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alcoholates.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The term "substituted" preferably relates to the substitution by the above-mentioned substituents, where a plurality of different degrees of substitution is possible, unless indicated otherwise.

All physiologically acceptable salts, derivatives, solvates, solvates of salts, and stereoisomers of these compounds, including mixtures thereof in all ratios, are also in accordance with the invention.

The invention relates to the compounds of the formula I and salts thereof and to a process for the preparation of compounds of the formula I and pharmaceutically acceptable salts, solvates, solvates of salts, tautomers or stereoisomers, including mixtures thereof in all ratios thereof, characterised in that a) a compound of the formula (II)

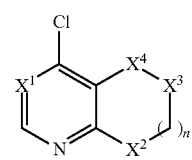

in which $X^1$, $X^2$, $X^3$, $X^4$ and n have the meanings indicated in formula I,
is reacted with a compound of the formula (III)

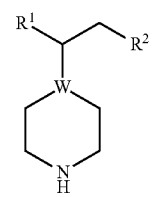

in which W, $R^1$ and $R^2$ have the meanings indicated in formula I,
or
b) for the preparation of compounds of the formula I, wherein $X^3$ is CO and $X^4$ is NH,
a compound of the formula (IV)

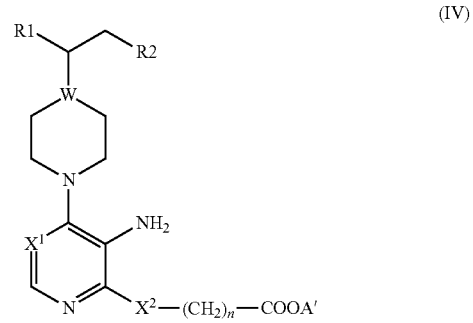

in which $R^1$, $R^2$, W, $X^1$, $X^2$ and n have the meanings indicated in formula I, and A' is alkyl with 1, 2, 3 or 4 C-atoms,
is cyclised,
and/or
a base or acid of the formula I is converted into one of its salts.

Above and below, the radicals $R^1$, $R^2$, W, $X^1$, $X^2$, $X^3$, $X^4$ and n have the meanings indicated for the formula I, unless expressly stated otherwise.

"A" denotes alkyl, this is unbranched (linear) or branched, and has 1, 2, 3, 4, 5, 6, 7, 8, 9 or 10 C atoms. "A" preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

"A" very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, "A" denotes e.g. $CH_2OCH_3$, $CH_2CH_2OH$, $OCH_2CH_2NH_2$, $CH_2NHCH_3$ or $NHCH_2CH_3$.

Cyc preferably denotes cyclopropyl, cyclobutyl, cyclopentyl, cyclohexyl or cycloheptyl.

$R^1$ preferably denotes Ar.

$R^3$ preferably denotes H or alkyl having 1, 2, 3 or 4 C atoms, particularly preferably H or methyl.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyano-phenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3, 5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl which is unsubstituted or mono- or disubstituted by Hal and/or A.

Ar particularly preferably denotes phenyl which is monosubstituted by $CF_3$, F or Cl.

Het preferably denotes pyridyl or pyrimidyl, which is unsubstituted or monosubstituted by "A".

$Het^1$ preferably denotes pyrrolidinyl, azetidinyl or piperidinyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ie, which conform to the formula I and in which the radicals not designated in greater detail have the meaning indicated for the formula I, but in which in Ia $R^3$ is H or methyl;
in Ib Ar is phenyl which is unsubstituted or mono- or disubstituted by Hal and/or A;
in Ic Het is pyridyl or pyrimidyl, which is unsubstituted or monosubstituted by A;
in Id $Het^1$ is pyrrolidinyl, azetidinyl or piperidinyl;
in
Ie $X^1$ is N or CH,
$X^2$ is $CH_2$ or NH,
$X^3$ is $CH_2$ or CO,
$X^4$ is $CH_2$ or NH,
$R^1$ is Ar,
$R^2$ is $[C(R^3)_2]_p Het^1$ or $[C(R^3)_2]_p N(R^3)_2$,
$R^3$ is H or methyl,
Ar is phenyl which is unsubstituted or mono- or disubstituted by Hal and/or A,
$Het^1$ is pyrrolidinyl, azetidinyl or piperidinyl,
A is unbranched or branched alkyl with 1-10 C-atoms, wherein one or two non-adjacent CH- and/or $CH_2$- groups may be replaced by N- and/or O-atoms and wherein 1-7H-atoms may be replaced by F or Cl, or Cyc,
Cyc is cyclic alkyl with 3-7 C-atoms,
Hal is F, Cl, Br or I,
each n is independently 0 or 1,
each p is independently 0, 1, 2, 3 or 4;
and pharmaceutically acceptable salts, solvates, solvates of salts, tautomers or stereoisomers, including mixtures thereof in all ratios thereof.

In certain embodiments of any of the forumulae presented herein, $R^1$ is

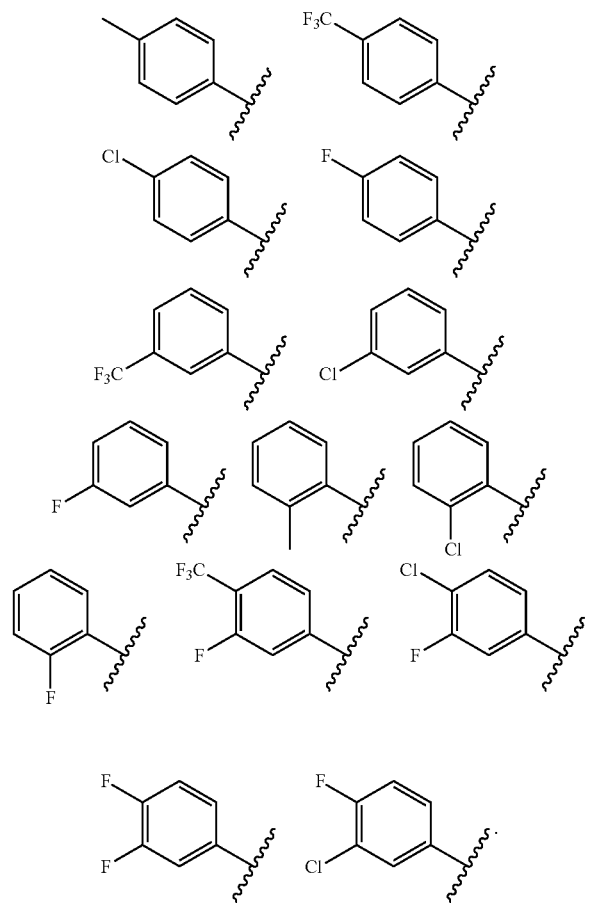

In certain embodiments of any of the forumulae presented herein, $R^2$ is

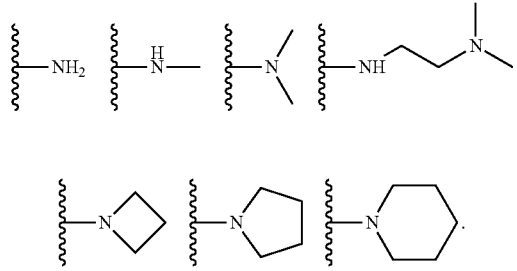

In certain embodiments, of any of the forumulae presented herein the ring

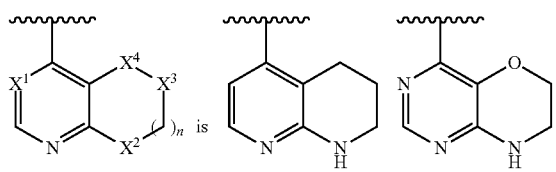

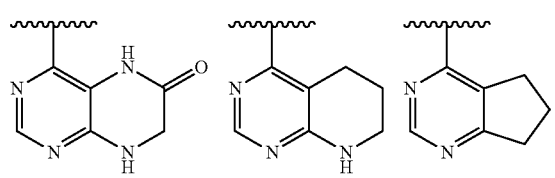

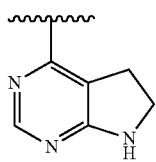

In certain embodiments, the invention provides a compound of formula I-f:

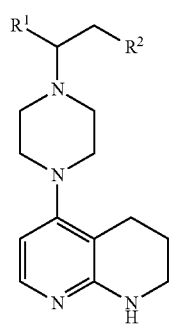

I-f and pharmaceutically acceptable salts, solvates, solvates of salts, tautomers or stereoisomers, including mixtures thereof in all ratios thereof;
wherein $R^1$ and $R^2$ are as defined above.

In certain embodiments, the invention provides a compound of formula I-g:

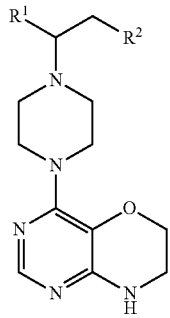

I-g and pharmaceutically acceptable salts, solvates, solvates of salts, tautomers or stereoisomers, including mixtures thereof in all ratios thereof;
wherein $R^1$ and $R^2$ are as defined above.

In certain embodiments, the invention provides a compound of formula I-h:

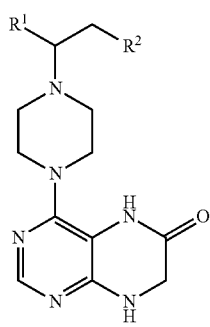

I-h and pharmaceutically acceptable salts, solvates, solvates of salts, tautomers or stereoisomers, including mixtures thereof in all ratios thereof;
wherein $R^1$ and $R^2$ are as defined above.

In certain embodiments, the invention provides a compound of formula I-i:

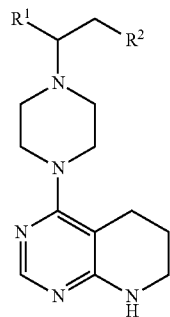

I-i and pharmaceutically acceptable salts, solvates, solvates of salts, tautomers or stereoisomers, including mixtures thereof in all ratios thereof;
wherein $R^1$ and $R^2$ are as defined above.

In certain embodiments, the invention provides a compound of formula I-j:

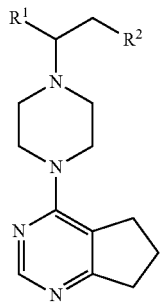

I-j and pharmaceutically acceptable salts, solvates, solvates of salts, tautomers or stereoisomers, including mixtures thereof in all ratios thereof;
wherein $R^1$ and $R^2$ are as defined above.

In certain embodiments, the invention provides a compound of formula I-k:

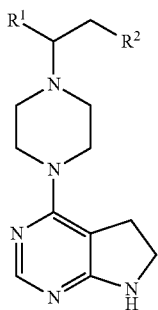

I-k and pharmaceutically acceptable salts, solvates, solvates of salts, tautomers or stereoisomers, including mixtures thereof in all ratios thereof;
wherein $R^1$ and $R^2$ are as defined above.

In certain embodiments of any of formulae I-f to I-k, $R^1$ is

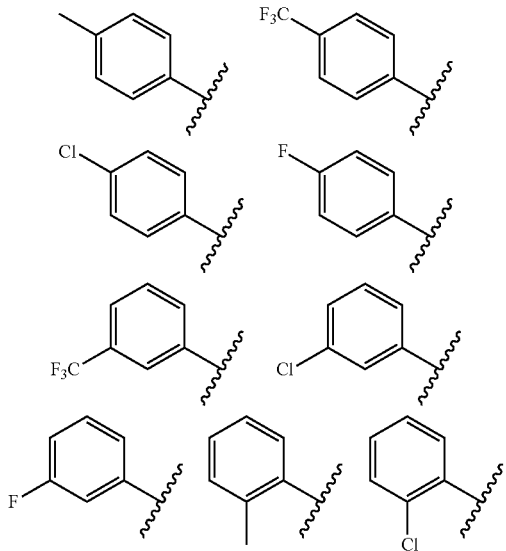

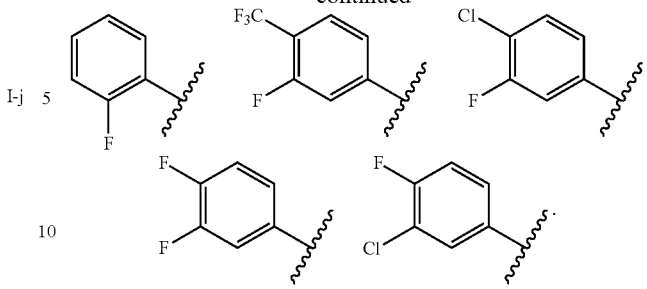

In certain embodiments of any of formulae I-f to I-k, $R^2$ is

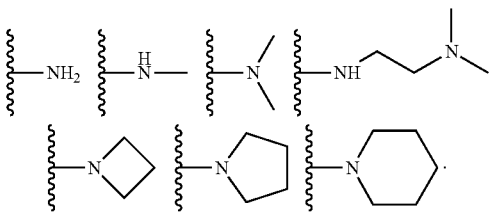

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise Use can also be made here of variants known per se which are not mentioned here in greater detail.

The starting compounds of the formulae II and III are generally known. If they are novel, however, they can be prepared by methods known per se.

Compounds of the formula I can preferably be obtained by reacting a compound of the formula II with a compound of the formula III.

Moreover, compounds of the formula I can preferably be obtained by cyclizing a compound of the formula IV.

The reaction is generally carried out under conditions known to the skilled artisan and which are known and suitable for the said reaction.

Depending on the conditions used, the reaction time is between a few minutes and 14 days, the reaction temperature is between about 0° and 160°, normally between 20° and 1500, in particular between about 60° and about 140°.

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to DMF, DMSO or NMP.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxy-methyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}O$, $^{14}O$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Inco-poration of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2$-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzene-sulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. A method for the resolution of racemates containing ester groups (for example acetyl esters) is the use of enzymes, in particular esterases.

Furthermore, the present invention relates to pharmaceutical compositions comprising at least one compound of the formula I and/or pharmaceutically acceptable salts, solvates, tautomers and stereoisomers thereof, including mixtures thereof in all ratios, and optionally excipients and/or adjuvants "Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

Exemplary disorders treated by the compounds of the invention include prostate cancer, thyroid cancer, liver cancer, lung cancer, breast cancer, colon cancer, prostate cancer, pituitary tumors, carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma; hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

In certain embodiments, the disorder is bladder cancer, breast cancer, cervical cancer, colon cancer, epidermis cancer, gall bladder cancer, kidney cancer, liver cancer, lung cancer, pituitary tumors, oesophagus cancer, ovarian cancer, pancreatic cancer, prostate cancer, stomach cancer, thyroid cancer, leukemia, B-cell lymphoma, T-cell lymphoma, Hodgkin's lymphoma, non-Hodgkin's lymphoma, hairy cell lymphoma, Burkett's lymphoma, acute and chronic myelogenous leukemias, myeloproliferative syndrome, myelodysplastic syndrome, promyelocytic leukemia; multiple myeloma, thyroid follicular cancer; astrocytoma, neuroblastoma, glioma, schwannoma, melanoma or Kaposi's sarcoma.

In certain embodiments, the disorder is multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma. In certain embodiments, the disorder is multiple myeloma, bladder cancer, cervical cancer, prostate cancer, thyroid carcinomas, lung cancer, breast cancer, or colon cancer.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

The disclosed compounds of the formula I can be administered in combination with other known therapeutic agents, including anticancer agents. As used here, the term "anti-cancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3] racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN- 1703[4]. ([1] Prop. INN (Proposed International Nonproprietary Name); [2] Rec. INN (Recommended International Nonproprietary Names); [3] USAN (United States Adopted Name); [4] no INN).

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils.

Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or/and pharmaceutically acceptable salts, solvates, solvates of salts, tautomers or stereoisomers, including mixtures thereof in all ratios thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

ABBREVIATIONS

| Designation | |
|---|---|
| ACN | acetonitrile |
| AcOH | Acetic acid |
| AIBN | Azobisisobutylonitrile |
| ATP | Adenosine triphosphate |
| b | Broad peak |
| Bop-Cl | Bis(2-oxo-3-oxazolidinyl)phosphinic chloride |
| Conc. | concentrated |
| d | Doublet |
| DCM | Dichloromethane |
| DCE | dichloroethane |
| DMAP | dimethylaminopyridine |
| DMF | dimethylformamide |
| DMSO | dimethylsulfoxide |
| DIEA/DIPEA | N,N-Diisopropylethylamine |
| DTT | dithiothreitol |
| EDTA | Ethylenediaminetetraacetic acid |
| equiv./eq. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| LiOH | Lithium hydroxide |
| m | multiplet |
| M | Molecular ion |
| m/z | Mass-to-charge ratio |
| Me | methyl |
| MeOH | methanol |
| min | minute |
| MS | Mass spectrometry |
| N | Normal (unit of concentration) |
| NaOH | Sodium hydroxide |
| NBS | N-bromosuccinimide |
| NMO | 4-methylmorpholine N-oxide |
| NMP | N-Methyl-2-pyrrolidone |
| NMR | Nuclear Magnetic Resonance |
| PG | Protecting group |
| psi | Pounds per square inch |
| q | Quartette (or quartet) |
| Rf | Retention factor |
| RT/rt | Room temperature |
| Rt. | Retention time |
| s | Singlet |
| T3P | Propylphosphonic anhydride |
| TBAF | Tetrabutylammonium fluoride |

-continued

| Designation | |
|---|---|
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) according to the hereinafter described schemes and working examples.

General synthetic scheme I

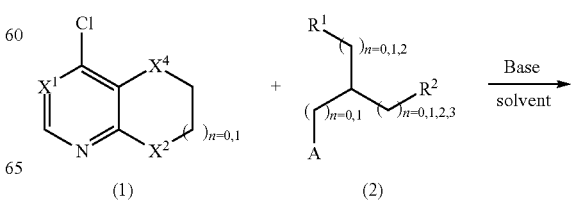

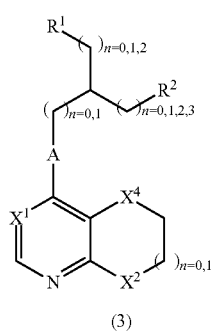

(3)

Bicyclic scaffolds (1) are reacted with amines (2) under basic condition to yield the compounds of Formula I (3). Unless otherwise designated the substituents in general synthetic scheme I correspond to those defined in Formula I.

General synthetic scheme II

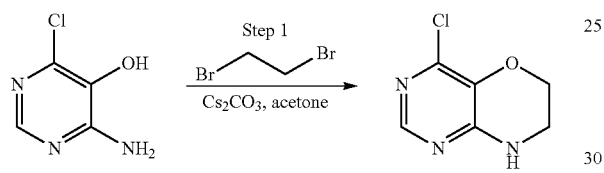

In some embodiments, the bicyclic scaffold was prepared from 4-amino-6-chloro-pyrimidin-5-ol reacting with 1,2-dibromo-ethane under basic conditions.

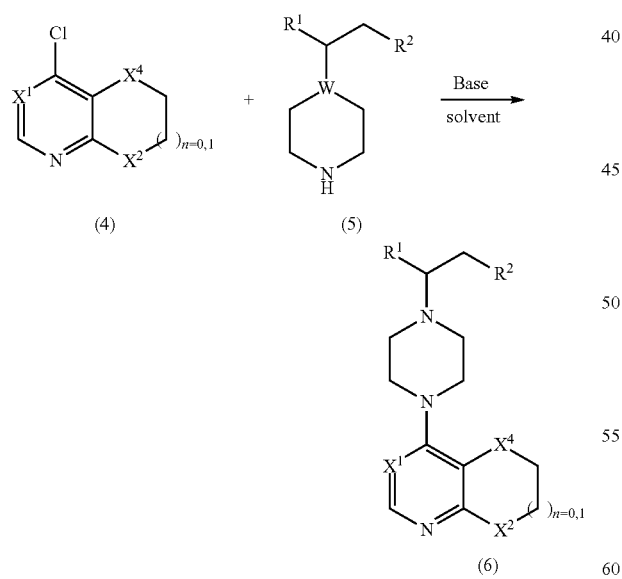

In a preferred embodiment, a bicyclic scaffold (4) is reacted with amine (5) (WO13/40044) under basic conditions to yield compound (6) also described by Formula I. Unless otherwise designated the substituents in general synthetic scheme II correspond to those defined in Formula I.

General synthetic scheme III

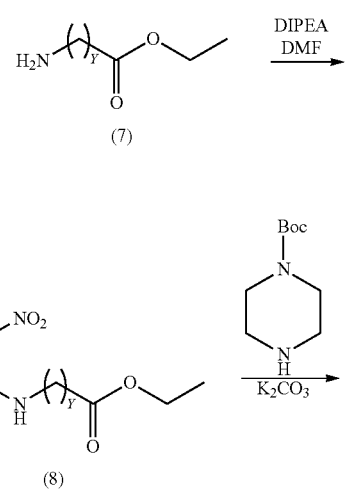

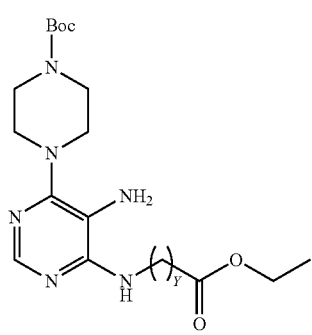

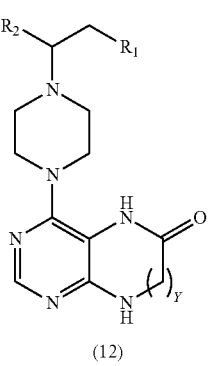

(12)

4,6-Dichloro-5-nitro-pyrimidine reacted with reagents (7) under basic condition to provide chloride intermediates (8). Chlorides (8) reacted with substituted amines to afford compounds (9). The bicyclic compounds (11) were obtained after de-boc of the ring closure product of compounds (10), which were yielded from the hydrogenation of compounds (9). The alkylation of compounds (11) in the presence of base afforded the desired compounds (12).

Analytical Methodology
Analytical LC/MS was Performed Using the Following Three Methods:

Method A: A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+mode with UV-detection at 254 and 280 nm with a gradient of 20-85% (B) in a 10 min linear gradient (11) hold for 1 min at 85% (B) (111) decrease from 20-85% (B) in a 0.2 min linear gradient (IV) hold for 3.8 min at 20% (B).

Method C: Gradient: 4.2 min/Flow: 2 ml/min 99:01-0:100 Water+0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC
Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC
Preparative HPLC was performed using either a Waters Atlantis dC18 OBD™ 10 μM (30×250 mm) column or a Waters Sunfire Prep $C_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.

Example 1

Compounds of Formula (I) according to General Synthetic Scheme II 2-(1-(5,6,7,8-tetrahydro-1,8-naphthyridin-4-yl)piperidin-4-yl)-2-(4-(trifluoromethyl)phenyl)ethanamine ("A1")

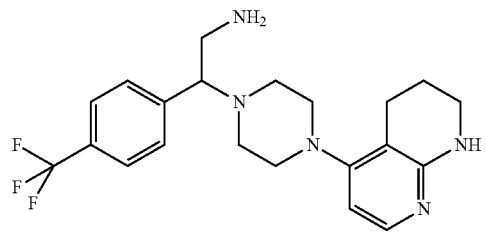 [SMILES: NCC(c1ccc(C(F)(F)F)cc1)N1CCN(c2ccnc3c2CCCN3)CC1]

Step 1: tert-butyl 4-(2-(4-nitrophenylsulfonamido)-1-(4-(trifluoromethyl)phenyl)-ethyl)piperidine-1-carboxylate To a solution of 4-[2-amino-1-(4-trifluoromethyl-phenyl)-ethyl]-piperazine-1-carboxylic acid tert-butyl ester (1000.00 mg; 2.68 mmol; 1.00 eq.) and diisopropylethylamine (0.58 ml; 3.21 mmol; 1.2 eq.) in 30 ml of DCM at 0° C., 4-nitro-benzenesulfonyl chloride (593.50 mg; 2.68 mmol; 1.0 eq.) was added. The resulting mixture was stirred at rt for 2 hrs. After removal of the solvent, the residue was subjected to snap column (eluted with 0-50% ethyl acetate in hexane) to afford tert-butyl 4-(2-(4-nitrophenylsulfonamido)-1-(4-(trifluoromethyl)phenyl)ethyl)piperidine-1-carboxylate (1050 mg, 70% yield).

Step 2: 4-nitro-N-(2-(piperidin-4-yl)-2-(4-(trifluoromethyl)phenyl)ethyl)-benzenesulfonamide A reaction mixture of tert-butyl 4-(2-(4-nitrophenylsulfonamido)-1-(4-(trifluoromethyl)phenyl)ethyl)piperidine-1-carboxylate (1050.0 mg; 1.88 mmol; 1.0 eq.) and 5 ml of 4M HCl in dioxane in 5 ml of methanol was stirred for 2 hr. After removal of the solvents, the residue was treated with ether, collected the white solid HCl salt of the title compound (814 mg, 81.5% yield).

Step 3: 4-nitro-N-(2-(1-(5,6,7,8-tetrahydropyrido[2,3-d]pyrimidin-4-yl)piperidin-4-yl)-2-(4-(trifluoromethyl)phenyl)ethyl)benzenesulfonamide A reaction mixture of 5-chloro-1,2,3,4-tetrahydro-[1,8] naphthyridine (50.0 mg; 0.3 mmol; 1.0 eq.), 4-nitro-N-(2-

(piperidin-4-yl)-2-(4-(trifluoromethyl)phenyl)ethyl)-benzenesulfonamide (157.56 mg; 0.30 mmol; 1.0 eq.) and diisopropylethylamine (0.27 ml; 1.5 mmol; 5.0 eq.) in 1 ml of NMP was stirred at 140° C. for 36 hrs. The crude was purified by pre-HPLC to afford the title compound (100 mg); LC-MS (M+H=590, obsd.=591).

Step 4: 2-(1-(5,6,7,8-tetrahydro-1,8-naphthyridin-4-yl)piperidin-4-yl)-2-(4-(trifluoromethyl)phenyl)ethanamine A reaction mixture of 4-nitro-N-[2-[4-(5,6,7,8-tetrahydro-[1,8]naphthyridin-4-yl)-piperazin-1-yl]-2-(4-trifluoromethyl-phenyl)-ethyl]-benzenesulfonamide (100.0 mg; 0.17 mmol; 1.0 eq.), benzenethiol (93.2 mg; 0.85 mmol; 5.0 eq.), and cesium carbonate (551.6 mg; 1.69 mmol; 10.0 eq.) in 5 ml of acetonitrile was stirred at 40° C. for 3 hrs. Little product was found by lc-ms, added another 0.1 ml of benzenethiol and stirred overnight. The crude was purified by pre-HPLC to afford the title compound as white solid (9.7 mg); LC-MS (M+H=405, obsd.=406).

2-(1-(2,3-dihydro-1H-pyrrolo[2,3-b]pyridin-4-yl)piperidin-4-yl)-2-(4-(trifluoro-methyl)phenyl)ethanamine ("A2")

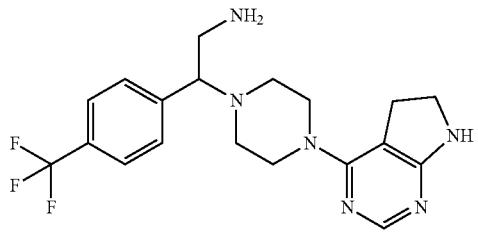 [SMILES: NCC(c1ccc(C(F)(F)F)cc1)N1CCN(c2ncnc3c2CCN3)CC1]

Step 1: 2-(1-(7-(4-methoxybenzyl)-6,7-dihydro-5H-pyrrolo[2,3-d]pyrimidin-4-yl)piperidin-4-yl)-2-(4-(trifluoromethyl)phenyl)ethanamine The reaction mixture of 4-chloro-7-(4-methoxy-benzyl)-6,7-dihydro-5H-pyrrolo[2,3-d]pyrimidine (60.0 mg; 0.22 mmol; 1.0 eq.), 2-(piperazin-1-yl)-2-(4-(trifluoromethyl)phenyl)ethanamine trihydrochloride (83.27 mg; 0.22 mmol; 1.0 eq.) and potassium carbonate (0.42 ml; 2.18 mmol; 10.0 eq.) in 1.5 ml of DMF was stirred at 120° C. for 60 hrs. The crude was purified by pre-HPLC to afford the title compound (50 mg, 31% yield); LC-MS (M+H=511, obsd.=512).

Step 2: 2-(1-(2,3-dihydro-1H-pyrrolo[2,3-b]pyridin-4-yl)piperidin-4-yl)-2-(4-(trifluoromethyl)phenyl)ethanamine To 2-(1-(7-(4-methoxybenzyl)-6,7-dihydro-5H-pyrrolo[2,3-d]pyrimidin-4-yl)piperidin-4-yl)-2-(4-(trifluoromethyl)phenyl)ethanamine bis(2,2,2-trifluoroacetate) (50.00 mg; 0.07 mmol; 1.00 eq.) in a sealed tube was added trifluoroacetic acid (1.00 ml; 8.77 mmol; 129.91 eq.), and the reaction mixture was stirred at 80° C. overnight. The crude was purified by pre-HPLC to afford the title product (5 mg, 11.9% yield); LC-MS (M+H=391, obsd.=392);
$^1$H NMR (400 MHz, DMSO-$d_6$) δ [ppm]: 7.19 (s, 1H), 6.82-6.84 (d, 2H), 6.57-6.59 (d, 2H), 3.09-3.29 (m, 1H), 3.07-3.09 (m, 4H), 2.93-2.97 (m, 3H), 2.93-2.99 (m, 3H), 1.87-1.91 (m, 2H), 1.24-1.59 (m, 2H).

2-(1-(6,7-dihydro-5H-cyclopenta[b]pyridin-4-yl)piperidin-4-yl)-2-(4-(trifluoromethyl)phenyl)ethanamine ("A3")

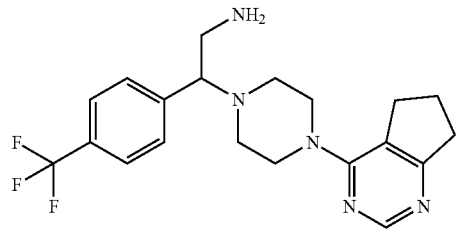 [SMILES: NCC(c1ccc(C(F)(F)F)cc1)N1CCN(c2ncnc3c2CCC3)CC1]

The reaction mixture of 4-chloro-6,7-dihydro-5H-cyclopentapyrimidine (50.0 mg; 0.32 mmol; 1.0 eq.), 2-(piperazin-1-yl)-2-(4-(trifluoromethyl)phenyl)ethanamine trihydrochloride (148.52 mg; 0.39 mmol; 1.20 eq.) and potassium carbonate (268.19 mg; 1.94 mmol; 6.0 eq.) in 1.5 ml of DMF was stirred at 120° C. overnight. The crude was purified by pre-HPLC to afford the title product (50 mg, 21% yield); LC-MS (M+H=390, obsd.=391);
$^1$H NMR (400 MHz, DMSO-$d_6$) δ [ppm]: 8.63 (s, 1H), 7.94-8.01 (d, 3H), 7.75-7.77 (d, 2H), 7.50-7.52 (d, 2H), 4.04-4.08 (m, 4H), 3.69-3.71 (m, 1H), 3.03-3.07 (m, 3H), 2.90-2.91 (m, 2H), 2.63-2.64 (m, 2H), 2.31-2.33 (m, 2H), 2.01-2.03 (m, 2H).

{2-(4-Chlorophenyl)-2-[4-(7,8-dihydro-6H-pyrimido[5,4-b][1,4]oxazin-4-yl)-piperazin-1-yl]-ethyl}-dimethylamine ("A4")

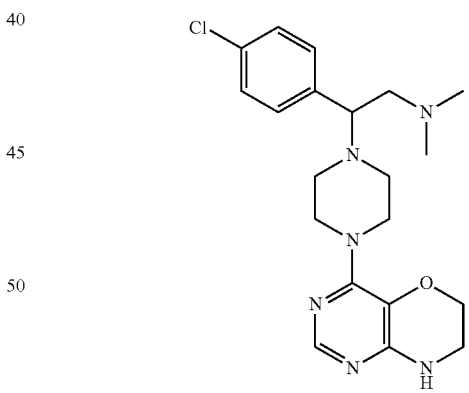

Step 1: 4-Chloro-7,8-dihydro-6H-pyrimido[5,4-b][1,4]oxazine

A reaction mixture of 4-amino-6-chloro-pyrimidin-5-ol (500.0 mg; 3.44 mmol; 1.0 eq.), cesium carbonate (2238 mg; 6.87 mmol; 2.0 eq.), and 1,2-dibromo-ethane (645.3 mg; 3.44 mmol; 1.0 eq.) in 10 ml of acetone was stirred at 65° C. for 14 hours. To the reaction solution was added 50 mL of ethyl acetate, washed with water, then brine and dried. The solvents were removed to give the residue, which was treated with ether, stirred for 30 min, filtered, to yield 4-chloro-7,8-dihydro-6H-pryrimido[5,4-b][1,4]oxazine as yellow solid (227 mg, 38.5% yield). LC-MS (M+H=172, obsd.=172/174).

Step 2: {2-(4-Chlorophenyl)-2-[4-(7,8-dihydro-6H-pyrimido[5,4-b][1,4]oxazin-4-yl)-piperazin-1-yl]-ethyl}-dimethylamine A mixture of [2-(4-Chloro-phenyl)-2-piperazin-1-yl-ethyl]-dimethyl-amine (300.0 mg; 1.03 mmol; 1.00 eq.), 4-Chloro-7,8-dihydro-6H-pyrimido[5,4-b][1,4]oxazine (196.49 mg; 1.13 mmol; 1.10 eq.) and potassium carbonate (363.37 mg; 2.58 mmol; 2.50 eq.) in DMSO (3.00 ml) was irradiated under microwave at 190° C. for 3 h. The reaction mixture was cooled to RT, diluted with water (20 mL), and extracted with DCM (3×20 mL). The combined organic layer was washed with brine solution, dried over $Na_2SO_4$ and concentrated under vacuum. The resulted brown thick residue was purified by biotage using DCM/MeOH as an elutent to yield brown gum. The gummy solid was triturated with diethylether (3 mL), filtered and dried under suction to afford the title compound as brown solid (36.00 mg, 8.2% yield). LC-MS (M+H=403, obsd.=403);

$^1$H NMR (400 MHz, DMSO-$d_6$) δ [ppm]: 7.63 (s, 1H), 7.37-7.35 (m, 2H), 7.29-7.26 (m, 2H), 6.98 (bs, 1H), 3.99 (t, J=4.2 Hz, 2H), 3.67 (bs, 1H), 3.44 (bs, 4H), 3.33 (bs, 2H), 2.75 (bs, 1H), 2.37 (bs, 4H), 2.10 (bs, 6H).

[2-[4-(7,8-Dihydro-6H-pyrimido[5,4-b][1,4]oxazin-4-yl)-piperazin-1-yl]-2-(4-trifluoromethylphenyl)-ethyl]-dimethylamine ("A5")

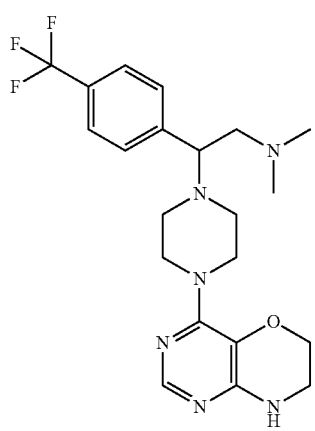 [SMILES: CN(C)CC(c1ccc(C(F)(F)F)cc1)N1CCN(c2ncnc3c2OCCN3)CC1]

The title compound was prepared according to the procedure described for the preparation of A4, using [2-(4-trifluoromethylphenyl)-2-piperazin-1-yl-ethyl]-dimethyl-amine as the starting material. LC-MS (M+H=437, obsd.=437);

$^1$H NMR (400 MHz, DMSO-$d_6$) δ [ppm]: 7.67 (d, J=7.4 Hz, 2H), 7.63 (s, 1H), 7.49 (d, J=8.1 Hz, 2H), 6.98 (bs, 1H), 3.99 (t, J=4.2 Hz, 2H), 3.76 (bs, 1H), 3.43-3.42 (m, 4H), 3.32 (bs, 2H), 2.81 (bs, 1H), 2.59 (bs, 1H), 2.39 (bs, 4H), 2.10 (bs, 6H).

[2-[4-(6,7-Dihydro-5H-pyrrolo[2,3-d]pyrimidin-4-yl)-piperazin-1-yl]-2-(4-trifluoromethylphenyl)-ethyl]-dimethylamine ("A6")

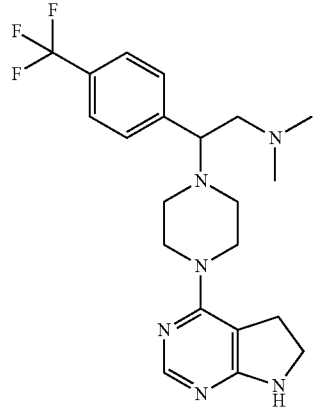 [SMILES: CN(C)CC(c1ccc(C(F)(F)F)cc1)N1CCN(c2ncnc3c2CCN3)CC1]

A mixture of dimethyl-[2-piperazin-1-yl-2-(4-trifluoromethyl-phenyl)-ethyl]-amine (300.00 mg; 0.96 mmol; 1.00 eq.), 4-Chloro-6,7-dihydro-5H-pyrrolo[2,3-d]pyrimidine (156.52 mg; 0.96 mmol; 1.00 eq.) and potassium carbonate (336.95 mg; 2.39 mmol; 2.50 eq.) in dry DMSO (3.00 ml) was irradiated at 190° C. for 3 h. The reaction mixture was cooled to RT, diluted with water (25 mL), and extracted with DCM (3×10 ml). The combined organic layer was washed with water, brine solution, dried over $Na_2SO_4$ and concentrated under vacuum. The resulted brown thick residue was purified by biotage using DCM/MeOH as an elutent to yield brown gum. This gum was further azeotroped with diethylether (2×10 ml) to obtain foamy solid. Then this solid was further treated with diethyl ether/hexane mixture (1:1, 5 ml). The solvent portion was syringed out and the remaining solid was further dried under vacuum to afford the title compound as pale brown solid (34.00 mg, 8.2% yield). LC-MS (M+H=421, obsd.=421);

$^1$H NMR (400 MHz, DMSO-$d_6$) δ [ppm]: 7.80 (s, 1H), 7.67 (d, J=7.7 Hz, 2H), 7.50 (d, J=8.1 Hz, 2H), 6.56 (bs, 1H), 3.76 (s, 1H), 3.50-3.48 (m, 4H), 3.37 (bs, 2H), 3.01 (t, J=8.6 Hz, 2H), 2.79 (bs, 2H), 2.50-2.49 (m, 1H), 2.39 (bs, 4H), 2.10 (bs, 6H).

{2-(4-Chlorophenyl)-2-[4-(6,7-dihydro-5H-pyrrolo[2,3-d]pyrimidin-4-yl)-piperazin-1-yl]-ethyl}-dimethylamine ("A7")

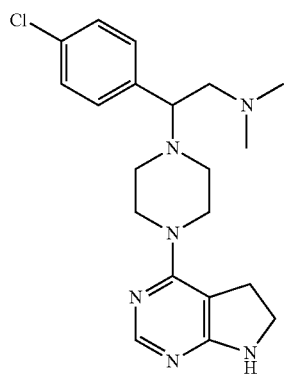 [SMILES: CN(C)CC(c1ccc(Cl)cc1)N1CCN(c2ncnc3c2CCN3)CC1]

The title compound was prepared according to the procedure described for the preparation of A6, using [2-(4-chlorophenyl)-2-piperazin-1-yl-ethyl]-dimethyl-amine as the starting material. LC-MS (M+H=7, obsd.=387);

¹H NMR (400 MHz, DMSO-d₆) δ [ppm]: 7.80 (s, 1H), 7.35 (d, J=8.4 Hz, 2H), 7.28 (d, J=8.5 Hz, 2H), 6.56 (bs, 1H), 3.66-3.63 (m, 1H), 3.51-3.43 (m, 4H), 3.37-3.36 (m, 2H), 3.01 (t, J=8.7 Hz, 2H), 2.73-2.66 (m, 1H), 2.60-2.57 (m, 1H), 2.40-2.32 (m, 4H), 2.09 (s, 6H).

{2-(4-Chlorophenyl)-2-[4-(5,6,7,8-tetrahydro-pyrido[2,3-d]pyrimidin-4-yl)-piperazin-1-yl]-ethyl}-dimethylamine ("A8")

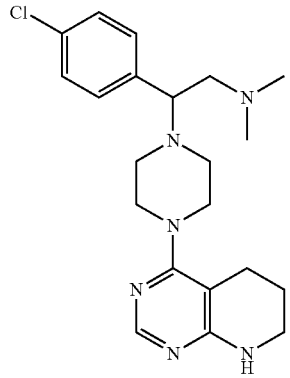 [SMILES: CN(C)CC(c1ccc(Cl)cc1)N1CCN(c2ncnc3c2CCCN3)CC1]

A mixture of [2-(4-Chloro-phenyl)-2-piperazin-1-yl-ethyl]-dimethyl-amine (300.00 mg; 1.03 mmol; 1.00 eq.), 4-Chloro-5,6,7,8-tetrahydro-pyrido[2,3-d]pyrimidine (184.01 mg; 1.03 mmol; 1.00 eq.) and potassium carbonate (363.37 mg; 2.58 mmol; 2.50 eq.) in dry DMSO (3.00 ml; 10.00 V) was irradiated at 190° C. for 3 h. The reaction mixture was cooled to RT, diluted with water (25 mL), and extracted with DCM (3×10 ml). The combined organic layer was washed with water, brine solution, dried over Na₂SO₄ and concentrated under vacuum. The resulted residue was purified by biotage using DCM/MeOH as an elutent to yield brown gum. This gum was further azeotroped with diethylether (2×10 ml) to obtain foamy solid. Then this solid was further treated with diethyl ether/hexane mixture (1:1, 5 ml), filtered and dried under suction to afford the title compound as pale brown solid (66.00 mg, 15.6% yield). LC-MS (M+H=401, obsd.=401);

¹H NMR (400 MHz, DMSO-d₆) δ [ppm]: 7.87 (s, 1H), 7.37 (d, J=8.2 Hz, 2H), 7.29 (d, J=8.5 Hz, 2H), 6.86 (bs, 1H), 3.68 (bs, 1H), 3.17-3.15 (m, 2H), 3.10 (bs, 4H), 2.76 (bs, 1H), 2.37 (bs, 4H), 2.36-2.32 (m, 2H), 2.11 (bs, 6H), 1.62-1.59 (m, 2H).

Dimethyl-[2-[4-(5,6,7,8-tetrahydro-pyrido[2,3-d]pyrimidin-4-yl)-piperazin-1-yl]-2-(4-trifluoromethylphenyl)-ethyl]-amine ("A9")

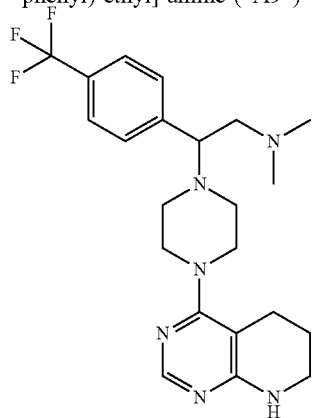

The title compound was prepared according to the procedure described for the preparation of A8, using [2-(4-trifluoromethylphenyl)-2-piperazin-1-yl-ethyl]-dimethyl-amine as the starting material. LC-MS (M+H=435, obsd.=435);

¹H NMR (400 MHz, DMSO-d₆) δ [ppm]: 7.87 (s, 1H), 7.68 (d, J=8.1 Hz, 2H), 7.51 (d, J=8.0 Hz, 2H), 6.87 (s, 1H), 3.79-3.75 (m, 1H), 3.16-3.15 (m, 2H), 3.10 (bs, 4H), 2.84-2.78 (m, 1H), 2.50-2.49 (m, 1H), 2.37-2.34 (m, 6H), 2.11 (s, 6H), 1.60 (bs, 2H).

2-[4-(7,8-Dihydro-6H-pyrimido[5,4-b][1,4]oxazin-4-yl)-piperazin-1-yl]-2-(4-trifluoromethylphenyl)-ethylamine ("A10")

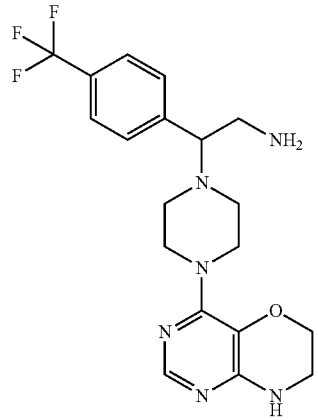 [SMILES: NCC(c1ccc(C(F)(F)F)cc1)N1CCN(c2ncnc3c2OCCN3)CC1]

A mixture of 2-piperazin-1-yl-2-(4-trifluoromethylphenyl)-ethylamine dihydrochloride (500 mg; 1.1 mmol; 1.0 eq.), 4-chloro-7,8-dihydro-6H-pyrimido[5,4-b][1,4]oxazine (200 mg; 1.1 mmol; 1.0 eq.) and potassium carbonate (804 mg; 5.7 mmol; 5.0 eq.) in dry DMSO (5.0 ml) was heated to 100° C. for 3 days. The reaction mixture was cooled to RT, diluted with water (100 mL) and extracted with DCM (2×100 mL). The combined organic layer was washed further with water (50 mL), brine solution, dried over Na2SO4 and concentrated under vacuum. The resulted residue was purified by Biotage eluting with DCM in MeOH; the resultant product was further purified by Prep.HPLC to afford the title compound as yellow solid (14.0 mg; 2.9% yield). LC-MS (M+H=409, obsd.=409);

¹H NMR (400 MHz, DMSO-d₆) δ [ppm]: 7.69 (d, J=8.1 Hz, 2H), 7.64 (s, 1H), 7.47 (d, J=8.0 Hz, 2H), 7.00 (s, 1H), 3.99 (t, J=4.2 Hz, 2H), 3.98-3.43 (m, 7H), 3.07-3.02 (m, 1H), 2.84-2.79 (m, 1H), 2.37-2.32 (m, 4H), 1.55 (br s, 1H).

2-(4-Chlorophenyl)-2-[4-(7,8-dihydro-6H-pyrimido[5,4-b][1,4]oxazin-4-yl)-piperazin-1-yl]-ethylamine ("A11")

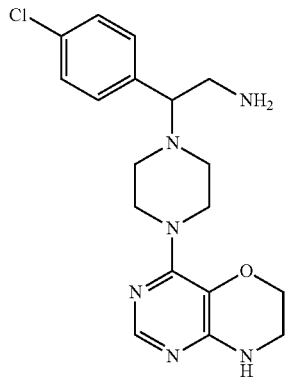 [SMILES: NCC(c1ccc(Cl)cc1)N1CCN(c2ncnc3c2OCCN3)CC1]

The title compound was prepared according to the procedure described for the preparation of A10, using 2-(4-chlorophenyl)-2-piperazin-1-yl-ethylamine dihydrochloride as the starting material. LC-MS (M+H=375, obsd.=375);

$^1$H NMR (400 MHz, DMSO-d$_6$) δ [ppm]: 7.63 (s, 1H), 7.38 (d, J=8.4 Hz, 2H), 7.26 (d, J=8.4 Hz, 2H), 6.99 (br s, 1H), 3.99 (t, J=4.3 Hz, 2H), 3.49-3.48 (m, 1H), 3.47-3.45 (m, 4H), 3.40-3.38 (m, 2H), 3.06-3.01 (m, 1H), 2.77-2.72 (m, 1H), 2.39-2.30 (m, 5H).

[2-[4-(7,8-Dihydro-6H-pyrimido[5,4-b][1,4]oxazin-4-yl)-piperazin-1-yl]-2-(3-fluoro-4-trifluoromethyl-phenyl)-ethyl]-dimethylamine ("A12")

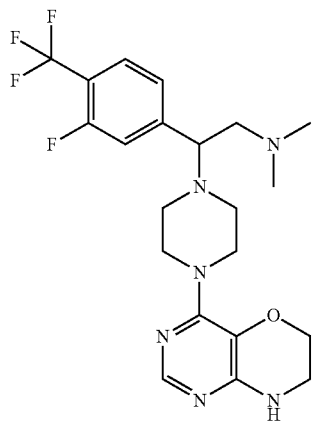 [SMILES: CN(C)CC(c1ccc(C(F)(F)F)c(F)c1)N1CCN(c2ncnc3c2OCCN3)CC1]

The title compound was prepared according to the procedure described for the preparation of A4, using [2-(3-fluoro-4-trifluoromethyl-phenyl)-2-piperazin-1-yl-ethyl]-dimethylamine as the starting material. LC-MS (M+H=455, obsd.=455);

$^1$H NMR (400 MHz, DMSO-d$_6$) δ [ppm]: 7.77 (d, J=6.2 Hz, 1H), 7.74 (s, 1H), 7.46 (d, J=12.0 Hz, 1H), 7.32 (d, J=8.0 Hz, 1H), 7.00 (s, 1H), 3.99 (t, J=4.2 Hz, 3H), 3.47 (s, 4H), 3.00 (br s, 2H), 2.45-2.44 (m, 4H), 2.37 (br s, 6H).

2-(4-Chloro-phenyl)-2-[4-(6,7-dihydro-5H-pyrrolo[2,3-d]pyrimidin-4-yl)-piperazin-1-yl]-ethylamine ("A13")

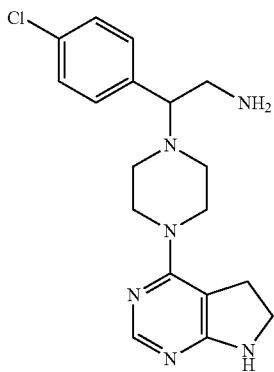 [SMILES: NCC(c1ccc(Cl)cc1)N1CCN(c2ncnc3c2CCN3)CC1]

The title compound was prepared according to the procedure described for the preparation of A10, using 2-(4-chlorophenyl)-2-piperazin-1-yl-ethylamine dihydrochloride and 4-chloro-6,7-dihydro-5H-pyrrolo[2,3-d]pyrimidine as the starting materials. LC-MS (M+H=359, obsd.=359);

$^1$H NMR (400 MHz, DMSO-d$_6$) δ [ppm]: 7.80 (s, 1H), 7.38 (d, J=8.4 Hz, 2H), 7.26 (d, J=8.4 Hz, 2H), 6.57 (br s, 1H), 3.51-3.49 (m, 5H), 3.49-3.48 (m, 1H), 3.04-2.99 (m, 3H), 2.78-2.73 (m, 1H), 2.37-2.32 (m, 5H), 1.69 (br s, 2H).

2-[4-(6,7-Dihydro-5H-pyrrolo[2,3-d]pyrimidin-4-yl)-piperazin-1-yl]-2-(4-fluorophenyl)-ethylamine ("A14")

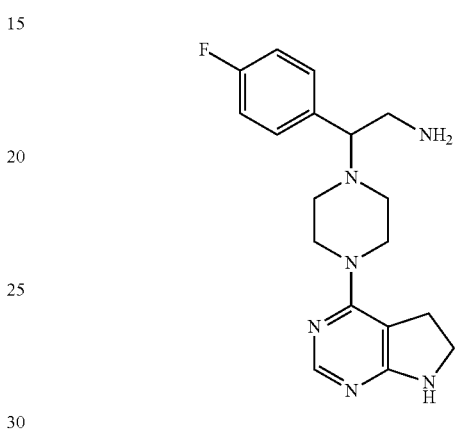

The title compound was prepared according to the procedure described for the preparation of A13, using 2-(4-fluorophenyl)-2-piperazin-1-yl-ethylamine dihydrochloride as the starting material. LC-MS (M+H=343, obsd.=343);

{2-(4-Chloro-3-fluoro-phenyl)-2-[4-(6,7-dihydro-5H-pyrrolo[2,3-d]pyrimidin-4-yl)-piperazin-1-yl]-ethyl}-dimethylamine ("A15")

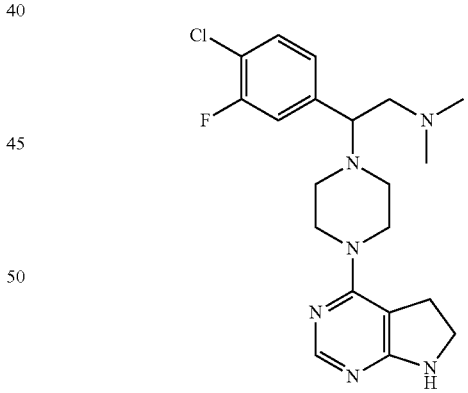

The title compound was prepared according to the procedure described for the preparation of A13, using [2-(4-chloro-3-fluoro-phenyl)-2-piperazin-1-yl-ethyl]-dimethylamine as the starting material. LC-MS (M+H=405, obsd.=405);

$^1$H NMR (400 MHz, DMSO-d$_6$) δ [ppm]: 7.80 (s, 1H), 7.51 (t, J=8.00 Hz, 1H), 7.34 (dd, J=1.72, 10.68 Hz, 1H), 7.14 (dd, J=1.68, 8.26 Hz, 1H), 6.57 (s, 1H), 3.73 (s, 1H), 3.48 (dd, J=4.16, Hz, 4H), 3.39-3.40 (m, 2H), 3.02 (t, J=8.88 Hz, 2H), 2.74-2.78 (m, 1H), 2.50-2.55 (m, 1H), 2.37 (s, 4H), 2.11 (s, 6H).

2-[4-(5,6,7,8-Tetrahydro-pyrido[2,3-d]pyrimidin-4-yl)-piperazin-1-yl]-2-(4-trifluoromethyl-phenyl)-ethylamine ("A16")

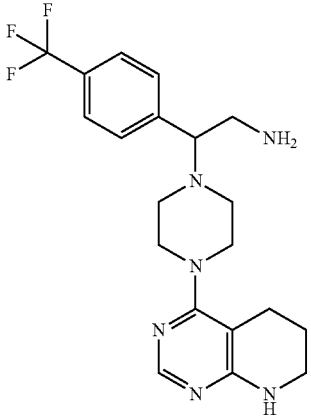

The title compound was prepared according to the procedure described for the preparation of A10, using 4-chloro-5,6,7,8-tetrahydro-pyrido[2,3-d]pyrimidine as the starting material. LC-MS (M+H=407, obsd.=407);

$^1$H NMR (400 MHz, DMSO-d$_6$) δ [ppm]: 7.88 (s, 1H), 7.70 (d, J=8.1 Hz, 2H), 7.49 (d, J=7.9 Hz, 2H), 6.88 (s, 1H), 3.48 (t, J=6.5 Hz, 2H), 3.17-3.13 (m, 6H), 3.13-3.03 (m, 1H), 2.84-2.79 (m, 2H), 2.41-2.32 (m, 5H), 1.62-1.61 (m, 3H).

2-(4-Chloro-phenyl)-2-[4-(5,6,7,8-tetrahydro-pyrido[2,3-d]pyrimidin-4-yl)-piperazin-1-yl]-ethylamine ("A17")

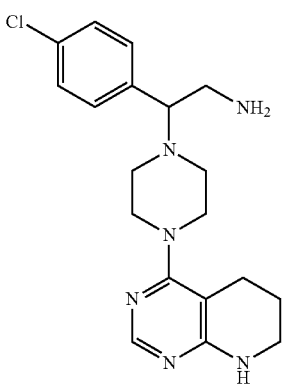 [SMILES: NCC(c1ccc(Cl)cc1)N1CCN(c2ncnc3c2CCCN3)CC1]

The title compound was prepared according to the procedure described for the preparation of A16, using 2-(4-chlorophenyl)-2-piperazin-1-yl-ethylamine dihydrochloride as the starting material. LC-MS (M+H=373, obsd.=373);

$^1$H NMR (400 MHz, DMSO-d$_6$) δ [ppm]: 7.87 (s, 1H), 7.39 (d, J=8.4 Hz, 2H), 7.27 (d, J=8.4 Hz, 2H), 6.87 (br s, 1H), 3.40-3.37 (m, 1H), 3.17-3.15 (m, 2H), 3.15-3.12 (m, 4H), 3.05-3.00 (m, 1H), 2.41-2.35 (m, 6H), 1.62-1.59 (m, 4H).

{2-(4-Chloro-3-fluoro-phenyl)-2-[4-(5,6,7,8-tetrahydro-pyrido[2,3-d]pyrimidin-4-yl)-piperazin-1-yl]-ethyl}-dimethylamine ("A18")

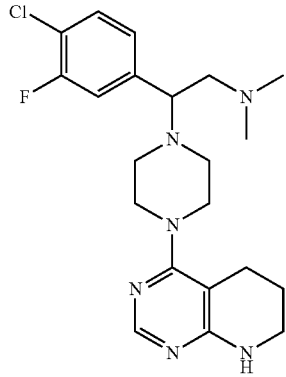 [SMILES: CN(C)CC(c1ccc(Cl)c(F)c1)N1CCN(c2ncnc3c2CCCN3)CC1]

The title compound was prepared according to the procedure described for the preparation of A16, using [2-(4-chloro-3-fluoro-phenyl)-2-piperazin-1-yl-ethyl]-dimethylamine as the starting material. LC-MS (M+H=419, obsd.=419);

{2-(3-Fluoro-4-trifluoromethyl-phenyl)-2-[4-(5,6,7,8-tetrahydro-pyrido[2,3-d]pyrimidin-4-yl)-piperazin-1-yl]-ethyl}-dimethylamine ("A19")

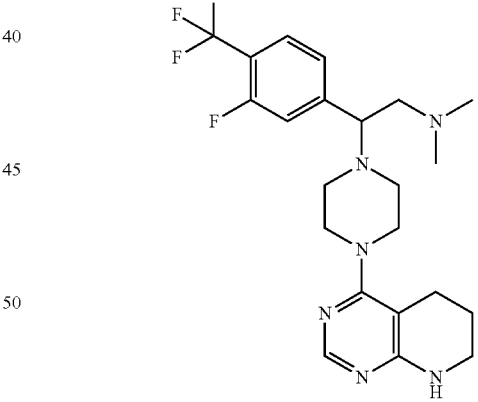

The title compound was prepared according to the procedure described for the preparation of A16, using [2-(3-fluoro-4-trifluoromethyl-phenyl)-2-piperazin-1-yl-ethyl]-dimethylamine as the starting material. LC-MS (M+H=453, obsd.=453);

$^1$H NMR (400 MHz, DMSO-d$_6$) δ [ppm]: 7.87 (s, 1H), 7.73 (t, J=7.8 Hz, 1H), 7.46 (d, J=12.1 Hz, 1H), 7.34 (d, J=8.2 Hz, 1H), 6.87 (s, 1H), 3.82 (s, 1H), 3.17-3.11 (m, 6H), 2.86 (t, J=9.8 Hz, 1H), 2.38-2.35 (m, 6H), 2.11 (s, 6H), 1.61 (t, J=4.68 Hz, 2H).

[2-[4-(6,7-Dihydro-5H-pyrrolo[2,3-d]pyrimidin-4-yl)-piperazin-1-yl]-2-(3-fluoro-4-trifluoromethyl-phenyl)-ethyl]-dimethylamine ("A20")

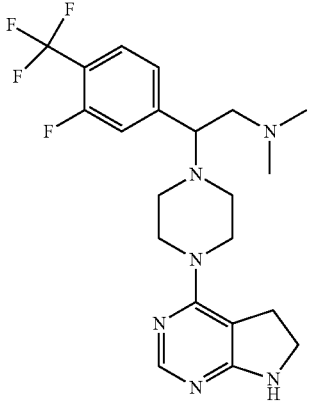 [SMILES: CN(C)CC(c1ccc(C(F)(F)F)c(F)c1)N1CCN(c2ncnc3c2CCN3)CC1]

The title compound was prepared according to the procedure described for the preparation of A6, using [2-(3-fluoro-4-trifluoromethyl-phenyl)-2-piperazin-1-yl-ethyl]-dimethyl-amine as the starting material. LC-MS (M+H=439, obsd.=439);

$^1$H NMR (400 MHz, DMSO-d$_6$) δ [ppm]: 7.80 (s, 1H), 7.71 (t, J=7.9 Hz, 1H), 7.45 (d, J=12.0 Hz, 1H), 7.33 (d, J=8.1 Hz, 1H), 6.58 (s, 1H), 3.82-3.79 (m, 1H), 3.49 (t, J=3.8 Hz, 4H), 3.37-3.33 (m, 2H), 3.04-3.00 (m, 2H), 2.86-2.81 (m, 1H), 2.50-2.48 (m, 1H), 2.40-2.38 (m, 4H), 2.10 (s, 6H).

2-(4-Fluoro-phenyl)-2-[4-(5,6,7,8-tetrahydro-pyrido[2,3-d]pyrimidin-4-yl)-piperazin-1-yl]-ethylamine ("A21")

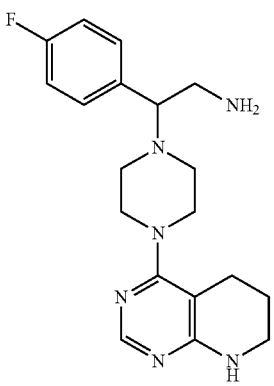 [SMILES: NCC(c1ccc(F)cc1)N1CCN(c2ncnc3c2CCCN3)CC1]

The title compound was prepared according to the procedure described for the preparation of A16, using 2-(4-fluorophenyl)-2-piperazin-1-yl-ethylamine dihydrochloride as the starting material. LC-MS (M+H=357, obsd.=357);

2-[1-(5,6,7,8-Tetrahydro-pyrido[2,3-d]pyrimidin-4-yl)-piperidin-4-yl]-2-(4-trifluoromethyl-phenyl)-ethylamine ("A22")

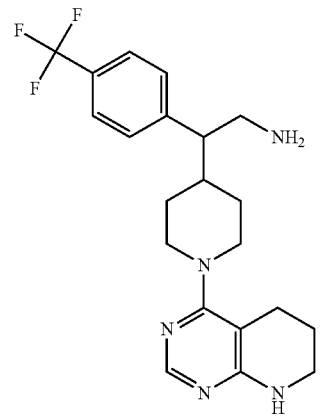 [SMILES: NCC(c1ccc(C(F)(F)F)cc1)C1CCN(c2ncnc3c2CCCN3)CC1]

The title compound was prepared according to the procedure described for the preparation of A16, using 2-piperidin-4-yl-2-(4-trifluoromethyl-phenyl)-ethylamine trihydrochloride as the starting material. LC-MS (M+H=406, obsd.=406);

$^1$H NMR (400 MHz, DMSO-d$_6$) δ [ppm]: 7.99 (s, 1H), 7.66 (s, 2H), 7.42-7.40 (d, J=8.0 Hz, 2H), 6.82 (s, 1H), 3.65-3.61 (d, J=12.6 Hz, 1H), 3.51-3.33 (m, 1H), 3.18 (s, 2H), 2.99-2.84 (m, 1H), 2.82-2.50 (m, 1H), 2.40-2.37 (m, 4H), 1.89-1.86 (d, J=12.28 Hz, 2H), 1.79-1.77 (d, J=8.48 Hz, 2H), 1.63-1.61 (d, J=10.48 Hz, 2H), 1.33-1.22 (m, 3H), 1.05-1.02 (m, 1H).

2-[1-(7,8-Dihydro-6H-pyrimido[5,4-b][1,4]oxazin-4-yl)-piperidin-4-yl]-2-(4-trifluoromethyl-phenyl)-ethylamine ("A23")

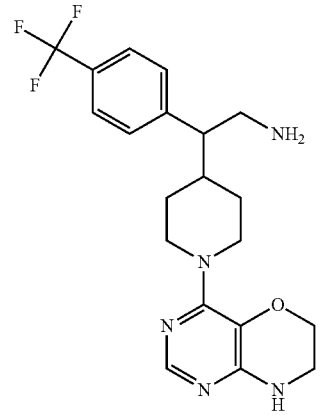 [SMILES: NCC(c1ccc(C(F)(F)F)cc1)C1CCN(c2ncnc3c2OCCN3)CC1]

The title compound was prepared according to the procedure described for the preparation of A10, using 2-piperidin-4-yl-2-(4-trifluoromethyl-phenyl)-ethylamine trihydrochloride as the starting material. LC-MS (M+H=408, obsd.=408);

$^1$H NMR (400 MHz, DMSO-d$_6$) δ [ppm]: 7.66-7.63 (m, 1H), 7.41-7.39 (d, J=8.1 Hz, 2H), 6.9 (s, 1H), 4.29-4.27 (d, 1H), 4.17-4.14 (d, 1H), 4.00-3.98 (m, 2H), 2.98-2.88 (m, 1H), 2.85-2.82 (m, 1H), 2.71-2.66 (m, 3H), 1.88-1.81 (m, 2H), 1.23-1.23 (m, 3H), 1.01-0.93 (m, 1H), 0.87-0.85 (m, 1H).

Example Compounds of Formula (I) According to General Synthetic Scheme III

4-{4-[2-dimethylamino-1-(4-fluoro-phenyl)-ethyl]-piperazin-1-yl}-7,8-dihydro-5H-pteridin-6-one ("A24")

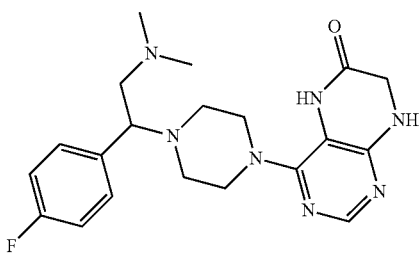 [SMILES: CN(C)CC(c1ccc(F)cc1)N1CCN(c2ncnc3c2NC(=O)CN3)CC1]

Step 1:
(6-chloro-5-nitro-pyrimidin-4-ylamino)-acetic acid ethyl ester

To amino-acetic acid ethyl ester hydrochloride (1439.15 mg; 10.31 mmol; 1.00 eq.) and 4,6-Dichloro-5-nitro-pyrimidine (2000.00 mg; 10.31 mmol; 1.00 eq.) in dry DMF (26 mL) was added ethyl-diisopropyl-amine (3997.72 mg; 30.93 mmol; 3.00 eq.) and the mixture was stirred for 3 hours. LC-MS showed that the reaction was complete. The DMF was removed and the EtOAc was added. The mixture was washed with brine, dried over MgSO4 and purified through flash chromatography on silica (EtOAc in Hexane from 0% to 30%) to provide (6-chloro-5-nitro-pyrimidin-4-ylamino)-acetic acid ethyl ester 2.1 g with 78% yield; LC/MS: 261 (M+H).

Step 2: 4-[6-(ethoxycarbonylmethyl-amino)-5-nitro-pyrimidin-4-yl]-piperazine-1-carboxylic acid tert-butyl ester The mixture of piperazine-1-carboxylic acid tert-butyl ester (800.00 mg; 4.30 mmol; 1.00 eq.), (6-chloro-5-nitro-pyrimidin-4-ylamino)-acetic acid ethyl ester (1119.49 mg; 4.30 mmol; 1.00 eq.) and potassium carbonate (1.78 g; 12.89 mmol; 3.00 eq.) in anhydrous DMF (5 mL) was stirred at 60° C. for 5 hours. LC/MS showed the reaction was complete. After pouring to the water, the solid was precipitated, filtered and dried, 1.4 g in 79% yield; LC-MS (M+1: 411, obsd: 411).

Step 3: 4-[5-amino-6-(ethoxycarbonylmethyl-amino)-pyrimidin-4-yl]-piperazine-1-carboxylic acid tert-butyl ester The mixture of 4-[6-(ethoxycarbonylmethyl-amino)-5-nitro-pyrimidin-4-yl]-piperazine-1-carboxylic acid tert-butyl ester (1400.00 mg; 3.41 mmol; 1.00 eq.) and Pd/C (300 mg) in MeOH (30 mL) was hydrogenated under 20 psi for 2 hours. After filtration, the solvent was removed and the crude was used for the next reaction (1.0 g, 77% yield); LC-MS (M+1: 381, obsd: 381).

Step 4:
4-piperazin-1-yl-7,8-dihydro-5H-pteridin-6-one hydrochloride

The solution of 4-[5-amino-6-(ethoxycarbonylmethyl-amino)-pyrimidin-4-yl]-piperazine-1-carboxylic acid tert-butyl ester (700.00 mg; 1.84 mmol; 1.00 eq.) in EtOH (20 mL) was refluxed for 15 hours. After concentration, the crude product was obtained and used for the next reaction.

The above crude product was suspended in 10 mL HCl in dioxane (4.0 M) and stirred for 1 h. LC/MS showed that the reaction was complete. After removal of the solvent, ether was added and the solid was filtered and dried; 400 mg in 80% in yield; LC-MS (M+1: 235, obsd: 235).

Step 5: 4-{4-[2-dimethylamino-1-(4-fluoro-phenyl)-ethyl]-piperazin-1-yl}-7,8-dihydro-5H-pteridin-6-one A mixture of [2-chloro-2-(4-fluoro-phenyl)-ethyl]-dimethyl-amine hydrochloride (50.00 mg; 0.21 mmol; 1.00 eq.), 4-piperazin-1-yl-7,8-dihydro-5H-pteridin-6-one hydrochloride (56.84 mg; 0.21 mmol; 1.00 eq.) and ethyl-diisopropyl-amine (0.19 ml; 1.05 mmol; 5.00 eq.) in CAN (5 mL) in the sealed vial was stirred at 70° C. for overnight. The product was purified through reverse phase HPLC. 18 mg in 21% yield; LC-MS (M+1: 400, obsd: 400);
$^1$H NMR (400 MHz, DMSO-d$_6$) δ [ppm]: 2.26 (6H), 2.63 (1H), 2.84 (1H), 2.88 (1H), 3.95 (2H), 4.14 (1H), 7.19 (2H), 7.27 (2H), 8.14 (1H).

4-{4-[2-dimethylamino-1-(3-fluoro-phenyl)-ethyl]-piperazin-1-yl}-7,8-dihydro-5H-pteridin-6-one ("A25")

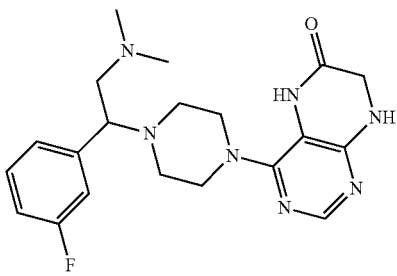 [SMILES: CN(C)CC(c1cccc(F)c1)N1CCN(c2ncnc3c2NC(=O)CN3)CC1]

The title compound was prepared according to the procedure described for the preparation of A24, using 2-chloro-2-(3-fluoro-phenyl)-ethyl]-dimethyl-amine hydrochloride as the starting material. LC-MS: (M+1=400, obsd.=400);
$^1$H NMR (400 MHz, DMSO-d$_6$) δ [ppm]: 2.27 (6H), 2.65 (1H), 2.86 (1H), 2.87 (1H), 3.98 (2H), 4.16 (1H), 6.83 (1H), 7.06 (2H), 7.38 (1H), 8.14 (1H).

4-{4-[2-dimethylamino-1-(4-chloro-phenyl)-ethyl]-piperazin-1-yl}-7,8-dihydro-5H-pteridin-6-one ("A26")

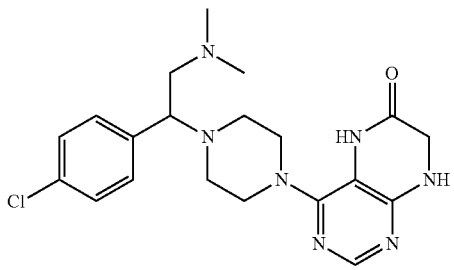 [SMILES: CN(C)CC(c1ccc(Cl)cc1)N1CCN(c2ncnc3c2NC(=O)CN3)CC1]

The title compound was prepared according to the procedure described for the preparation of A24, using 2-chloro-2-(4-chloro-phenyl)-ethyl]-dimethyl-amine hydrochloride as the starting material. LC-MS: (M+1=400, obsd.=400);

$^1$H NMR (400 MHz, DMSO-d$_6$) δ [ppm]: 2.24 (6H), 2.61 (1H), 2.82 (1H), 2.89 (1H), 3.95 (2H), 4.14 (1H), 7.44 (2H), 7.48 (2H), 8.14 (1H).

4-{4-[2-dimethylamino-1-(3-chloro-phenyl)-ethyl]-piperazin-1-yl}-7,8-dihydro-5H-pteridin-6-one ("A27")

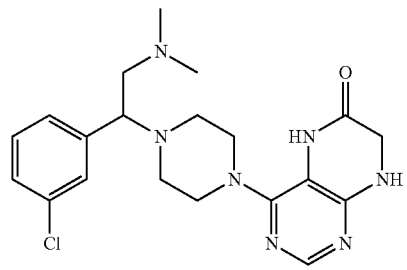 [SMILES: CN(C)CC(c1cccc(Cl)c1)N1CCN(c2ncnc3c2NC(=O)CN3)CC1]

The title compound was prepared according to the procedure described for the preparation of A24, using 2-chloro-2-(3-chloro-phenyl)-ethyl]-dimethyl-amine hydrochloride as the starting material. LC-MS: (M+1=400, obsd.=400);

$^1$H NMR (400 MHz, DMSO-d$_6$) δ [ppm]: 2.27 (6H), 2.65 (1H), 2.86 (1H), 2.87 (1H), 3.98 (2H), 4.16 (1H), 7.17 (1H), 7.31-7.34 (2H), 7.49 (1H), 8.14 (1H).

4-{4-[2-dimethylamino-1-(4-trifluoromethyl-phenyl)-ethyl]-piperazin-1-yl}-7,8-dihydro-5H-pteridin-6-one ("A28")

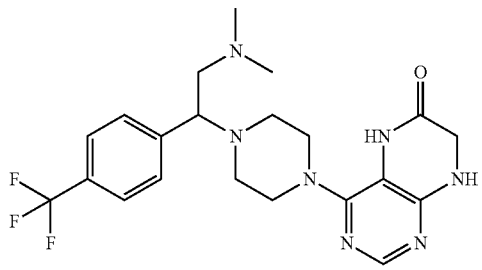 [SMILES: CN(C)CC(c1ccc(C(F)(F)F)cc1)N1CCN(c2ncnc3c2NC(=O)CN3)CC1]

The title compound was prepared according to the procedure described for the preparation of A24, using 2-chloro-2-(4-trifluoromethyl-phenyl)-ethyl]-dimethyl-amine hydrochloride as the starting material. LC-MS: (M+1=450, obsd.=450);

$^1$H NMR (400 MHz, DMSO-d$_6$) δ [ppm]: 2.26 (6H), 2.63 (1H), 2.84 (1H), 2.88 (1H), 3.95 (2H), 4.14 (1H), 7.22 (2H), 7.57 (2H), 8.14 (1H).

4-{4-[1-(4-fluoro-phenyl)-2-(pyrrolidin-yl)-ethyl]-piperazin-1-yl}-7,8-dihydro-5H-pteridin-6-one ("A29")

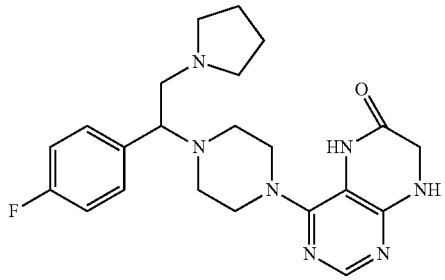 [SMILES: O=C1CNc2ncnc(N3CCN(C(CN4CCCC4)c4ccc(F)cc4)CC3)c2N1]

The title compound was prepared according to the procedure described for the preparation of A24, using 2-chloro-2-(4-fluoro-phenyl)-ethyl]-pyrrolidine hydrochloride as the starting material. LC-MS: (M+1=426, obsd.=426);

$^1$H NMR (400 MHz, DMSO-d$_6$) δ [ppm]: 1.68 (4H), 2.26 (4H), 2.63 (1H), 2.86 (1H), 2.89 (1H), 3.98 (2H), 4.16 (1H), 7.19 (2H), 7.28 (2H), 8.14 (1H).

4-{4-[1-(4-chloro-phenyl)-2-(pyrrolidin-yl)-ethyl]-piperazin-1-yl}-7,8-dihydro-5H-pteridin-6-one ("A30")

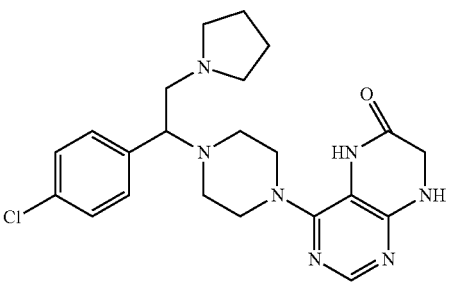 [SMILES: O=C1CNc2ncnc(N3CCN(C(CN4CCCC4)c4ccc(Cl)cc4)CC3)c2N1]

The title compound was prepared according to the procedure described for the preparation of A24, using 2-chloro-2-(4-chloro-phenyl)-ethyl]-pyrrolidine hydrochloride as the starting material. LC-MS: (M+1=442, obsd.=442);

$^1$H NMR (400 MHz, DMSO-d$_6$) δ [ppm]: 1.67 (4H), 2.26 (4H), 2.65 (1H), 2.80 (1H), 2.84 (1H), 3.98 (2H), 4.17 (1H), 7.44 (2H), 7.48 (2H), 8.14 (1H).

4-{4-[1-(4-fluoro-phenyl)-2-(piperidin-yl)-ethyl]-piperazin-1-yl}-7,8-dihydro-5H-pteridin-6-one ("A31")

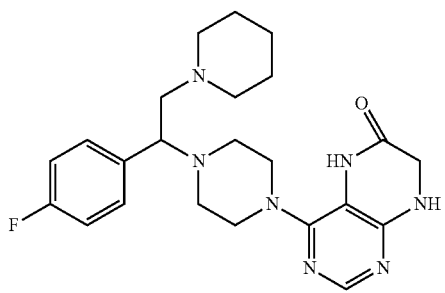 [SMILES: O=C1CNc2ncnc(N3CCN(C(CN4CCCCC4)c4ccc(F)cc4)CC3)c2N1]

The title compound was prepared according to the procedure described for the preparation of A24, using 2-chloro-2-(4-fluoro-phenyl)-ethyl]-piperidine hydrochloride as the starting material. LC-MS: (M+1=440, obsd.=440);

$^1$H NMR (400 MHz, DMSO-$d_6$) δ [ppm]: 1.53 (4H), 1.59 (2H), 2.46 (4H), 2.63 (1H), 2.86 (1H), 2.89 (1H), 3.98 (2H), 4.16 (1H), 7.19 (2H), 7.28 (2H), 8.14 (1H).

4-{4-[1-(4-chloro-phenyl)-2-(piperidin-yl)-ethyl]-piperazin-1-yl}-7,8-dihydro-5H-pteridin-6-one ("A32")

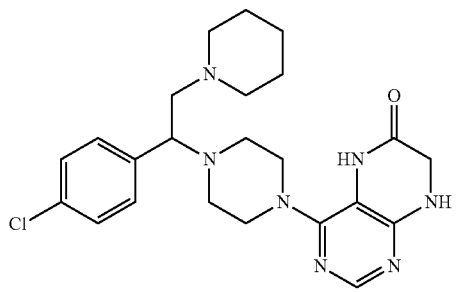 [SMILES: O=C1CNc2ncnc(N3CCN(C(CN4CCCCC4)c4ccc(Cl)cc4)CC3)c2N1]

The title compound was prepared according to the procedure described for the preparation of A24, using 2-chloro-2-(4-chloro-phenyl)-ethyl]-piperidine hydrochloride as the starting material. LC-MS: (M+1=457, obsd.=457);

$^1$H NMR (400 MHz, DMSO-$d_6$) δ [ppm]: 1.52 (4H), 1.60 (2H), 2.47 (4H), 2.62 (1H), 2.86 (1H), 2.89 (1H), 3.98 (2H), 4.16 (1H), 7.44 (2H), 7.48 (2H), 8.14 (1H).

4-{4-[1-(4-trifluoro-phenyl)-2-(piperidin-yl)-ethyl]-piperazin-1-yl}-7,8-dihydro-5H-pteridin-6-one ("A33")

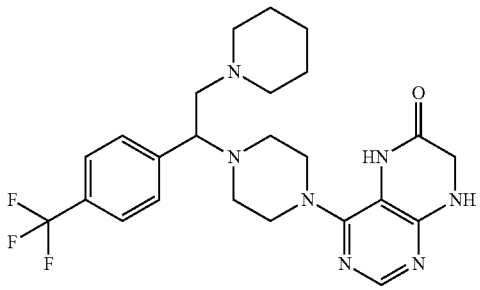 [SMILES: O=C1CNc2ncnc(N3CCN(C(CN4CCCCC4)c4ccc(C(F)(F)F)cc4)CC3)c2N1]

The title compound was prepared according to the procedure described for the preparation of A24, using 2-chloro-2-(4-trifluoro-phenyl)-ethyl]-piperidine hydrochloride as the starting material. LC-MS: (M+1=490, obsd.=490);

$^1$H NMR (400 MHz, DMSO-$d_6$) δ [ppm]: 1.50 (4H), 1.57 (2H), 2.43 (4H), 2.65 (1H), 2.85 (1H), 2.90 (1H), 3.98 (2H), 4.16 (1H), 7.26 (2H), 7.59 (2H), 8.14 (1H).

4-{4-[2-Pyrrolidin-1-yl-1-(4-trifluoromethyl-phenyl)-ethyl]-piperazin-1-yl}-7,8-dihydro-5H-pteridin-6-one ("A34")

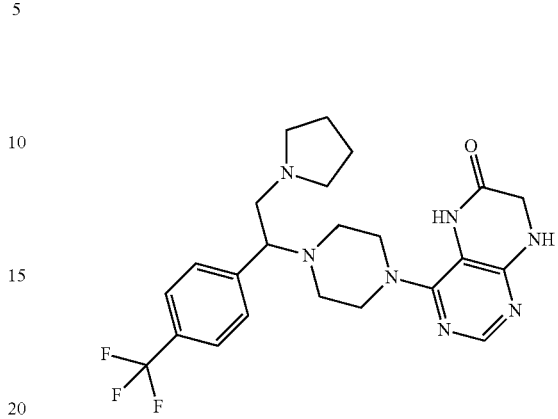

The title compound was prepared according to the procedure described for the preparation of A24, using 2-chloro-2-(4-trifluoromethyl-phenyl)-ethyl]-pyrrolidine hydrochloride as the starting material. LC-MS: (M+1=476, obsd.=476);

$^1$H NMR (400 MHz, DMSO-$d_6$) δ [ppm]: 1.68 (4H), 2.28 (4H), 2.66 (1H), 2.81 (1H), 2.86 (1H), 3.98 (2H), 4.17 (1H), 7.29 (2H), 7.63 (2H), 8.14 (1H).

4-(4-(1-(2-fluorophenyl)-2-(pyrrolidin-1-yl)ethyl)piperazin-1-yl)-7,8-dihydropteridin-6(5H)-one ("A35")

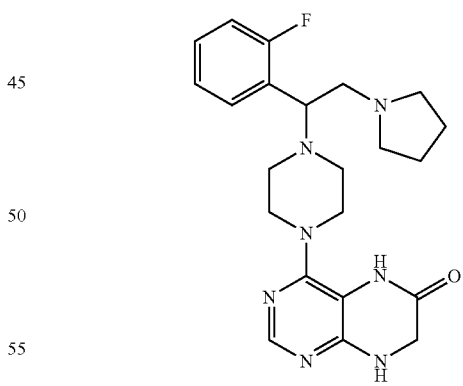

The title compound was prepared according to the procedure described for the preparation of A24, using 2-chloro-2-(2-chlorophenyl)-ethyl]-pyrrolidine hydrochloride as the starting material. LC-MS: (M+1=426, obsd.=426);

$^1$H NMR (400 MHz, DMSO-$d_6$) δ [ppm]: 7.72 (s, 1H), 7.38 (d, J=7.4 Hz, 1H), 7.28 (d, J=20.9 Hz, 1H), 7.14 (t, J=6.5 Hz, 1H), 7.05 (t, J=10.8 Hz, 1H), 3.94 (s, 3H), 3.13-3.02 (m, 5H), 2.89-2.85 (m, 1H), 2.56-2.54 (m, 4H), 2.40-2.37 (m, 4H), 2.29-2.28 (m, 4H).

4-(4-(2-(dimethylamino)-1-(2-fluorophenyl)ethyl)piperazin-1-yl)-7,8-dihydropteridin-6(5H)-one ("A36")

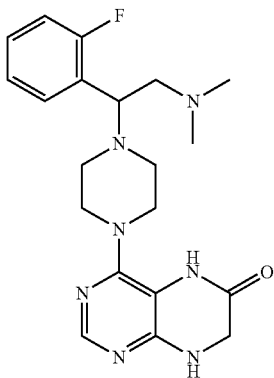 [SMILES: CN(C)CC(c1ccccc1F)N1CCN(c2ncnc3c2NC(=O)CN3)CC1]

The title compound was prepared according to the procedure described for the preparation of A24, using 2-chloro-2-(2-fluorophenyl)-N,N-dimethylethanamine hydrochloride as the starting material. LC-MS: (M+1=400, obsd.=400);

$^1$H NMR (400 MHz, DMSO-d$_6$) δ [ppm]: 9.63 (s, 1H), 7.81 (s, 1H), 7.36 (t, J=7.0 Hz, 2H), 7.28 (s, 1H), 7.23 (d, J=7.1 Hz, 2H), 3.79 (s, 5H), 3.33 (s, 1H), 3.19 (s, 6H), 2.66 (s, 1H), 2.59 (s, 2H), 2.49 (t, J=1.60 Hz, 2H), 2.32 (s, 2H).

4-(4-(2-(azetidin-1-yl)-1-(2-fluorophenyl)ethyl)piperazin-1-yl)-7,8-dihydropteridin-6(5H)-one "A37")

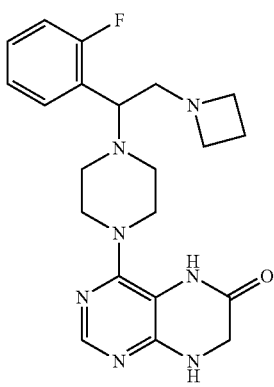 [SMILES: O=C1CNc2ncnc(N3CCN(C(CN4CCC4)c4ccccc4F)CC3)c2N1]

The title compound was prepared according to the procedure described for the preparation of A24, using 1-(2-chloro-2-(2-fluorophenyl)-ethyl)-azetidine hydrochloride as the starting material. LC-MS: (M+1=412, obsd.=412);

$^1$H NMR (400 MHz, DMSO-d$_6$) δ [ppm]: 9.57 (s, 1H), 7.83 (s, 1H), 7.44-7.40 (m, 1H), 7.26 (dd, J=11.5, 16.2 Hz, 2H), 7.17-7.09 (m, 2H), 3.79 (t, J=1.2 Hz, 3H), 3.12-3.02 (m, 8H), 2.50-2.48 (m, 5H), 2.35-2.31 (m, 1H), 1.90 (t, J=6.8 Hz, 2H).

4-(4-(1-(2-fluorophenyl)-2-(piperidin-1-yl)ethyl)piperazin-1-yl)-7,8-dihydropteridin-6(5H)-one ("A38")

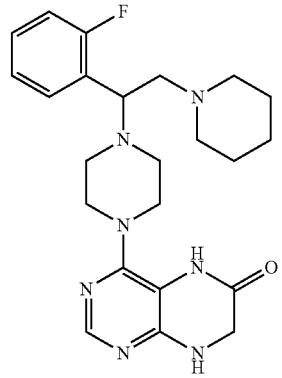 [SMILES: O=C1CNc2ncnc(N3CCN(C(CN4CCCCC4)c4ccccc4F)CC3)c2N1]

The title compound was prepared according to the procedure described for the preparation of A24, using 1-(2-chloro-2-(2-fluorophenyl)-ethyl)-piperidine hydrochloride as the starting material. LC-MS: (M+1=440, obsd.=440);

$^1$H NMR (400 MHz, DMSO-d$_6$) δ [ppm]: 9.61 (s, 1H), 7.81 (s, 1H), 7.37 (t, J=6.7 Hz, 1H), 7.28 (d, J=8.1 Hz, 2H), 7.15 (dd, J=7.1, 17.1 Hz, 2H), 4.04 (t, J=7.0 Hz, 1H), 3.78 (s, 2H), 3.16 (s, 4H), 2.66 (s, 3H), 2.49 (s, 3H), 2.30 (t, J=10.68 Hz, 2H), 1.31 (s, 8H).

4-(4-(2-amino-1-(2-chlorophenyl)ethyl)piperazin-1-yl)-7,8-dihydropteridin-6(5H)-one ("A39")

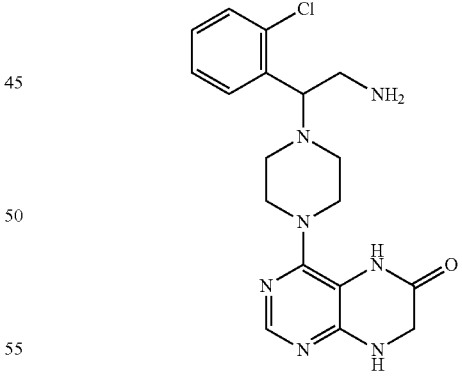

The title compound was prepared according to the procedure described for the preparation of A24, using 2-chloro-2-(2-chlorophenyl)-ethanamine hydrochloride as the starting material. LC-MS: (M+1=388, obsd.=388);

$^1$H NMR (400 MHz, DMSO-d$_6$) δ [ppm]: 9.62 (s, 1H), 7.86 (s, 1H), 7.75 (dd, J=1.5, 7.7 Hz, 1H), 7.38-7.30 (m, 3H), 7.26-7.22 (m, 1H), 4.50 (dd, J=3.5, 9.5 Hz, 1H), 3.82 (s, 2H), 3.25 (s, 5H), 2.69-2.66 (m, 1H), 2.50-2.48 (m, 1H), 2.32 (d, J=3.60 Hz, 1H), 2.25 (t, J=9.80 Hz, 2H).

4-(4-(1-(2-chlorophenyl)-2-(dimethylamino)ethyl)piperazin-1-yl)-7,8-dihydropteridin-6(5H)-one ("A40")

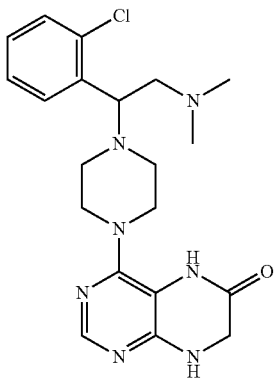 [SMILES: CN(C)CC(c1ccccc1Cl)N1CCN(c2ncnc3c2NC(=O)CN3)CC1]

The title compound was prepared according to the procedure described for the preparation of A24, using 2-chloro-2-(2-chlorophenyl)-N,N-dimethylethanamine hydrochloride as the starting material. LC-MS: (M+1=416, obsd.=416);

$^1$H NMR (400 MHz, DMSO-d$_6$) δ [ppm]: 9.62 (s, 1H), 7.82 (s, 1H), 7.46 (d, J=0.0 Hz, 2H), 7.35 (s, 1H), 7.31 (t, J=7.4 Hz, 2H), 4.22 (s, 1H), 3.79 (s, 2H), 3.15 (s, 4H), 2.59 (s, 2H), 2.49 (s, 4H), 2.12 (s, 6H).

4-(4-(1-(2-chlorophenyl)-2-(methylamino)ethyl)piperazin-1-yl)-7,8-dihydropteridin-6(5H)-one "A41"

The title compound was prepared according to the procedure described for the preparation of A24, using 2-chloro-2-(2-chlorophenyl)-N-methylethanamine hydrochloride as the starting material. LC-MS: (M+1=402, obsd.=402);

$^1$H NMR (400 MHz, DMSO-d$_6$) δ [ppm]: 9.63 (s, 1H), 8.17 (s, 1H), 7.86 (s, 1H), 7.66 (s, 1H), 7.64 (t, J=6.2 Hz, 1H), 7.42-7.31 (m, 1H), 7.29-7.25 (m, 2H), 4.20 (dd, J=4.4, 9.0 Hz, 1H), 3.82 (s, 2H), 3.29-3.24 (m, 4H), 3.19 (d, J=0.00 Hz, 2H), 2.50-2.49 (m, 2H), 2.38-2.31 (m, 2H), 2.19 (s, 3H).

4-(4-(2-(azetidin-1-yl)-1-(2-chlorophenyl)ethyl)piperazin-1-yl)-7,8-dihydropteridin-6(5H)-one ("A42")

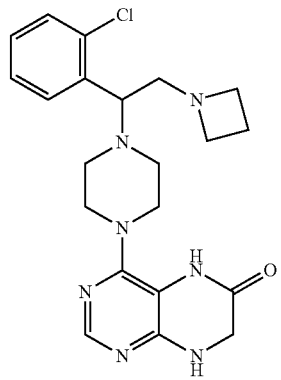 [SMILES: O=C1CNc2ncnc(N3CCN(C(CN4CCC4)c4ccccc4Cl)CC3)c2N1]

The title compound was prepared according to the procedure described for the preparation of A24, using 1-(2-chloro-2-(2-chlorophenyl)-ethyl)-azetidine hydrochloride as the starting material. LC-MS: (M+1=428, obsd.=428);

$^1$H NMR (400 MHz, DMSO-d$_6$) δ [ppm]: 9.77 (s, 1H), 7.93 (s, 1H), 7.66-7.59 (m, 2H), 7.49-7.45 (m, 3H), 5.15 (d, J=5.6 Hz, 1H), 4.18 (d, J=8.1 Hz, 2H), 4.04 (t, J=7.7 Hz, 2H), 3.87 (s, 2H), 3.28 (s, 4H), 2.89 (s, 1H), 2.77 (s, 2H), 2.50-2.48 (m, 3H), 2.36-2.30 (m, 2H).

4-(4-(1-(2-chlorophenyl)-2-(pyrrolidin-1-yl)ethyl)piperazin-1-yl)-7,8-dihydropteridin-6(5H)-one ("A43")

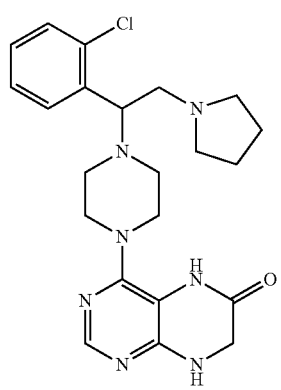 [SMILES: O=C1CNc2ncnc(N3CCN(C(CN4CCCC4)c4ccccc4Cl)CC3)c2N1]

The title compound was prepared according to the procedure described for the preparation of A24, using 1-(2-chloro-2-(2-chlorophenyl)-ethyl)-pyrrolidine hydrochloride as the starting material. LC-MS: (M+1=442, obsd.=442);

$^1$H NMR (400 MHz, DMSO-d$_6$) δ [ppm]: 9.62 (s, 1H), 7.82 (s, 1H), 7.47-7.41 (m, 2H), 7.33 (t, J=6.4 Hz, 1H), 7.26 (t, J=7.6 Hz, 2H), 4.21 (d, J=7.0 Hz, 1H), 3.79 (s, 2H), 3.15 (s, 4H), 2.93 (t, J=12.0 Hz, 1H), 2.79 (s, 1H), 2.66-2.60 (m, 2H), 2.50-2.49 (m, 8H), 1.59 (s, 4H).

4-(4-(1-(2-chlorophenyl)-2-(piperidin-1-yl)ethyl)
piperazin-1-yl)-7,8-dihydropteridin-6(5H)-one
("A44")

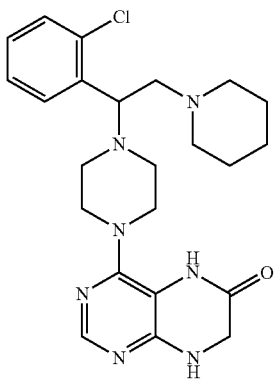

The title compound was prepared according to the procedure described for the preparation of A24, using 1-(2-chloro-2-(2-chlorophenyl)-ethyl)-piperidine hydrochloride as the starting material. LC-MS: (M+1=456, obsd.=456);

$^1$H NMR (400 MHz, DMSO-d$_6$) δ [ppm]: 9.62 (s, 1H), 7.82 (s, 1H), 7.47-7.40 (m, 1H), 7.32 (t, J=7.0 Hz, 1H), 7.27 (d, J=11.9 Hz, 3H), 4.18 (s, 1H), 3.79 (s, 2H), 3.15 (s, 4H), 2.71 (s, 1H), 2.67-2.61 (m, 4H), 2.32 (t, J=1.80 Hz, 4H), 1.43-0.00 (m, 7H).

4-(4-(2-(dimethylamino)-1-(o-tolyl)ethyl)piperazin-
1-yl)-7,8-dihydropteridin-6(5H)-one ("A45")

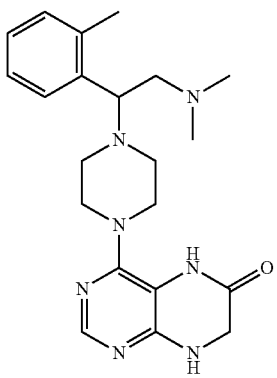 [SMILES: Cc1ccccc1C(CN(C)C)N1CCN(c2ncnc3c2NC(=O)CN3)CC1]

The title compound was prepared according to the procedure described for the preparation of A24, using 2-chloro-N,N-dimethyl-2-(o-tolyl)-ethanamine hydrochloride as the starting material. LC-MS: (M+1=396, obsd.=396);

$^1$H NMR (400 MHz, DMSO-d$_6$) δ [ppm]: 9.58 (s, 1H), 7.82 (s, 1H), 7.28 (s, 2H), 7.15 (s, 3H), 3.80 (d, J=1.2 Hz, 4H), 3.15 (s, 5H), 2.66 (t, J=1.8 Hz, 4H), 2.36 (s, 3H), 2.12 (s, 6H).

4-(4-(2-(pyrrolidin-1-yl)-1-(o-tolyl)ethyl)piperazin-
1-yl)-7,8-dihydropteridin-6(5H)-one ("A46")

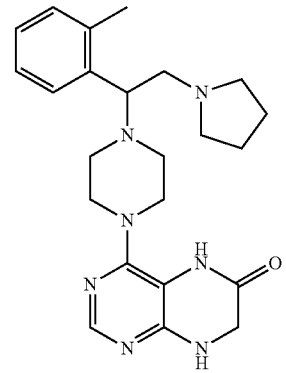 [SMILES: Cc1ccccc1C(CN1CCCC1)N1CCN(c2ncnc3c2NC(=O)CN3)CC1]

The title compound was prepared according to the procedure described for the preparation of A24, using 1-(2-chloro-2-(o-tolyl)ethyl)-pyrrolidine hydrochloride as the starting material. LC-MS: (M+1=422, obsd.=422);

$^1$H NMR (400 MHz, DMSO-d$_6$) δ [ppm]: 9.58 (s, 1H), 7.82 (s, 1H), 7.29 (d, J=12.6 Hz, 2H), 7.12 (d, J=14.5 Hz, 3H), 3.80 (s, 5H), 3.15 (s, 4H), 2.95 (s, 1H), 2.66 (s, 3H), 2.49 (t, J=1.7 Hz, 4H), 2.41 (s, 3H), 1.61 (s, 4H).

4-(4-(2-(piperidin-1-yl)-1-(o-tolyl)ethyl)piperazin-1-
yl)-7,8-dihydropteridin-6(5H)-one ("A47")

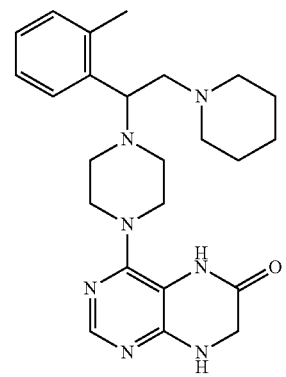 [SMILES: Cc1ccccc1C(CN1CCCCC1)N1CCN(c2ncnc3c2NC(=O)CN3)CC1]

The title compound was prepared according to the procedure described for the preparation of A24, using 1-(2-chloro-2-(o-tolyl)ethyl)-piperidine hydrochloride as the starting material. LC-MS: (M+1=436, obsd.=436);

$^1$H NMR (400 MHz, DMSO-d$_6$) δ [ppm]: 9.59 (s, 1H), 7.82 (s, 1H), 7.30 (d, J=10.9 Hz, 2H), 7.14-7.10 (m, 4H), 3.80 (s, 3H), 3.33 (s, 4H), 3.14 (s, 5H), 2.51-2.48 (m, 3H), 2.34 (s, 4H), 1.41 (s, 4H), 1.32 (s, 2H).

4-(4-(2-amino)-1-(3,4-difluorophenyl)ethyl)piperazin-1-yl)-7,8-dihydropteridin-6(5H)-one ("A48")

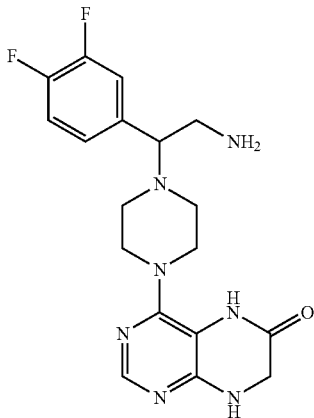 [SMILES: NCC(c1ccc(F)c(F)c1)N1CCN(c2ncnc3c2NC(=O)CN3)CC1]

The title compound was prepared according to the procedure described for the preparation of A24, using 2-chloro-2-(3,4-difluorophenyl)-ethanamine hydrochloride as the starting material. LC-MS: (M+1=390, obsd.=390);

$^1$H NMR (400 MHz, DMSO-d$_6$) δ [ppm]: 9.60 (s, 1H), 7.85 (s, 1H), 7.47-7.42 (m, 1H), 7.37-7.33 (m, 2H), 7.26 (d, J=31.5 Hz, 1H), 4.09-4.05 (m, 1H), 3.82 (s, 2H), 3.22 (s, 6H), 2.50-2.48 (m, 6H).

4-(4-(1-(3,4-difluorophenyl)-2-(dimethylamino)ethyl)piperazin-1-yl)-7,8-dihydropteridin-6(5H)-one ("A49")

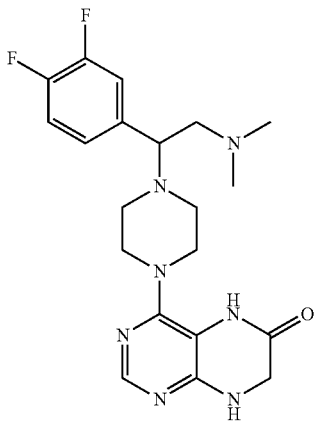

The title compound was prepared according to the procedure described for the preparation of A24, using 2-chloro-2-(3,4-difluorophenyl)-N,N-dimethylethanamine hydrochloride as the starting material. LC-MS: (M+1=418, obsd.=418);

$^1$H NMR (400 MHz, DMSO-d$_6$) δ [ppm]: 9.59 (s, 1H), 7.81 (s, 1H), 7.39-7.32 (m, 2H), 7.27 (s, 1H), 7.12 (s, 1H), 3.79 (s, 2H), 3.74-3.70 (m, 2H), 3.14 (d, J=3.6 Hz, 4H), 2.85-2.80 (m, 1H), 2.50-2.45 (m, 4H), 2.10 (s, 6H).

4-(4-(1-(3,4-difluorophenyl)-2-(methylamino)ethyl)piperazin-1-yl)-7,8-dihydropteridin-6(5H)-one ("A50")

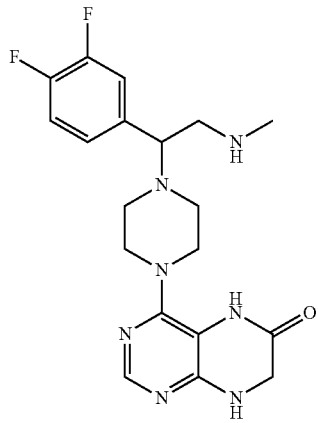 [SMILES: CNCC(c1ccc(F)c(F)c1)N1CCN(c2ncnc3c2NC(=O)CN3)CC1]

The title compound was prepared according to the procedure described for the preparation of A24, using 2-chloro-2-(3,4-difluorophenyl)-N-methyl-ethanamine hydrochloride as the starting material. LC-MS: (M+1=404, obsd.=404);

$^1$H NMR (400 MHz, DMSO-d$_6$) δ [ppm]: 9.61 (s, 1H), 8.28 (s, 1H), 7.85 (s, 1H), 7.40-7.30 (m, 3H), 7.19 (s, 1H), 3.82 (s, 2H), 3.68-3.65 (m, 1H), 3.23 (s, 4H), 2.66 (t, J=1.8 Hz, 2H), 2.50 (s, 3H), 2.26-2.22 (m, 1H), 2.14 (s, 3H).

4-(4-(2-(azetidin-1-yl)-1-(3,4-difluorophenyl)ethyl)piperazin-1-yl)-7,8-dihydropteridin-6(5H)-one "A51")

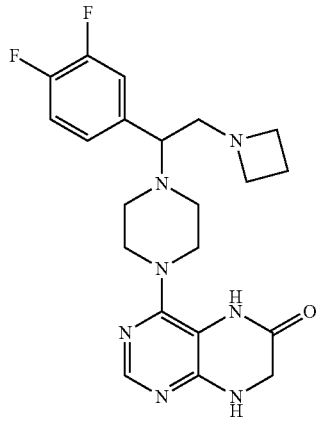 [SMILES: O=C1CNc2ncnc(N3CCN(C(CN4CCC4)c4ccc(F)c(F)c4)CC3)c2N1]

The title compound was prepared according to the procedure described for the preparation of A24, using 1-(2-chloro-2-(3,4-difluorophenyl)-ethyl)-azetidine hydrochloride as the starting material. LC-MS: (M+1=430, obsd.=430);

$^1$H NMR (400 MHz, DMSO-d$_6$) δ [ppm]: 7.97 (s, 1H), 7.40-7.31 (m, 2H), 7.25 (s, 1H), 4.06 (s, 4H), 3.54 (s, 1H), 3.45-3.23 (m, 8H), 3.09-3.07 (m, 1H), 3.00 (s, 1H), 2.34 (s, 6H).

4-(4-(1-(3,4-difluorophenyl)-2-(pyrrolidin-1-yl)ethyl)piperazin-1-yl)-7,8-dihydropteridin-6(5H)-one ("A52")

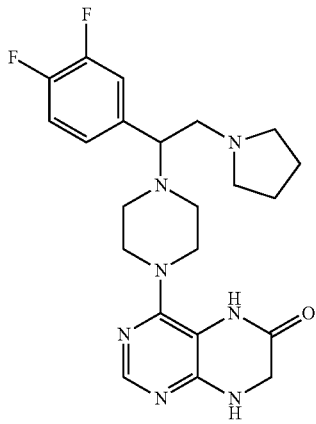 [SMILES: O=C1CNc2ncnc(N3CCN(C(CN4CCCC4)c4ccc(F)c(F)c4)CC3)c2N1]

The title compound was prepared according to the procedure described for the preparation of A24, using 1-(2-chloro-2-(3,4-difluorophenyl)-ethyl)-pyrrolidine hydrochloride as the starting material. LC-MS: (M+1=444, obsd.=444);

$^1$H NMR (400 MHz, DMSO-d$_6$) δ [ppm]: 7.74 (s, 1H), 7.25-7.11 (m, 3H), 3.99 (s, 2H), 3.66 (s, 1H), 3.11-3.02 (m, 4H), 2.89 (d, J=6.9 Hz, 2H), 2.62-2.55 (m, 4H), 2.38 (d, J=7.0 Hz, 4H), 1.63 (d, J=3.5 Hz, 4H).

4-(4-(1-(3,4-difluorophenyl)-2-(piperidin-1-yl)ethyl)piperazin-1-yl)-7,8-dihydropteridin-6(5H)-one "A53")

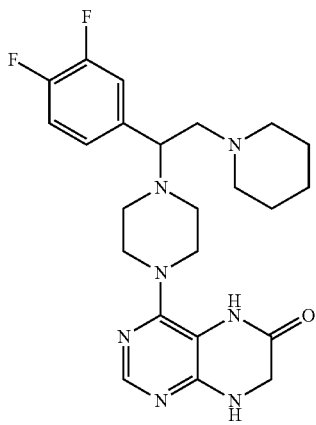 [SMILES: O=C1CNc2ncnc(N3CCN(C(CN4CCCCC4)c4ccc(F)c(F)c4)CC3)c2N1]

The title compound was prepared according to the procedure described for the preparation of A24, using 1-(2-chloro-2-(3,4-difluorophenyl)-ethyl)-piperidine hydrochloride as the starting material. LC-MS: (M+1=458, obsd.=458);

$^1$H NMR (400 MHz, DMSO-d$_6$) δ [ppm]: 9.60 (s, 1H), 7.82 (s, 1H), 7.37 (t, J=7.9 Hz, 2H), 7.28 (s, 1H), 7.13 (s, 1H), 3.79 (s, 3H), 3.15 (s, 4H), 2.65-2.64 (m, 3H), 2.40 (s, 2H), 2.29 (s, 3H), 1.32 (s, 8H).

4-(4-(1-(3-chloro-4-fluorophenyl)-2-(dimethylamino)ethyl)piperazin-1-yl)-7,8-dihydropteridin-6(5H)-one ("A54")

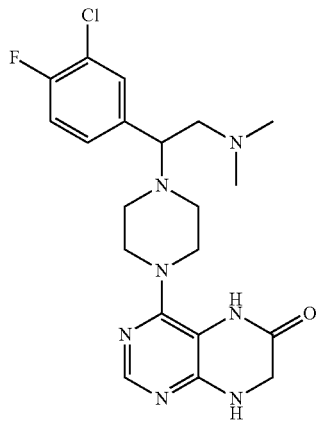 [SMILES: CN(C)CC(c1ccc(F)c(Cl)c1)N1CCN(c2ncnc3c2NC(=O)CN3)CC1]

The title compound was prepared according to the procedure described for the preparation of A24, using 2-chloro-2-(3-chloro-4-fluorophenyl)-N,N-dimethylethanamine hydrochloride as the starting material. LC-MS: (M+1=432, obsd.=432);

$^1$H NMR (400 MHz, DMSO-d$_6$) δ [ppm]: 9.60 (s, 1H), 7.81 (s, 1H), 7.51-7.49 (m, 1H), 7.38-7.30 (m, 1H), 7.29 (t, J=2.0 Hz, 2H), 3.77 (t, J=11.7 Hz, 4H), 3.15 (d, J=3.3 Hz, 5H), 2.86 (t, J=12.0 Hz, 1H), 2.50-2.45 (m, 3H), 2.12 (s, 6H).

4-(4-(2-(azetidin-1-yl)-1-(3-chloro-4-fluorophenyl)ethyl)piperazin-1-yl)-7,8-dihydropteridin-6(5H)-one ("A55")

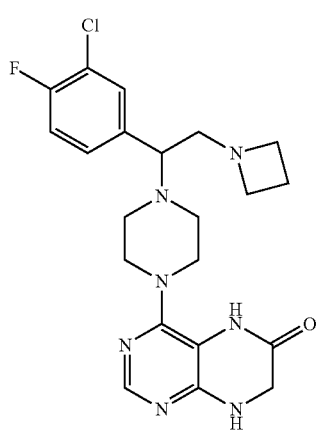 [SMILES: O=C1CNc2ncnc(N3CCN(C(CN4CCC4)c4ccc(F)c(Cl)c4)CC3)c2N1]

The title compound was prepared according to the procedure described for the preparation of A24, using 1-(2-chloro-2-(3-chloro-4-fluorophenyl)-ethyl)-azetidine hydrochloride as the starting material. LC-MS: (M+1=446, obsd.=446);

$^1$H NMR (400 MHz, DMSO-d$_6$) δ [ppm]: 9.71 (s, 1H), 7.90 (s, 1H), 7.73 (d, J=5.9 Hz, 1H), 7.59-7.51 (m, 5H), 4.81 (s, 1H), 4.09-4.02 (m, 4H), 3.86 (s, 2H), 3.04 (s, 4H), 2.75 (s, 2H), 2.50-2.48 (m, 2H), 2.32-2.26 (m, 2H).

4-(4-(1-(3-chloro-4-fluorophenyl)-2-(pyrrolidin-1-yl)ethyl)piperazin-1-yl)-7,8-dihydropteridin-6(5H)-one "A56")

4-(4-(1-(4-chloro-3-fluorophenyl)-2-(dimethylamino)ethyl)piperazin-1-yl)-7,8-dihydropteridin-6(5H)-one ("A58")

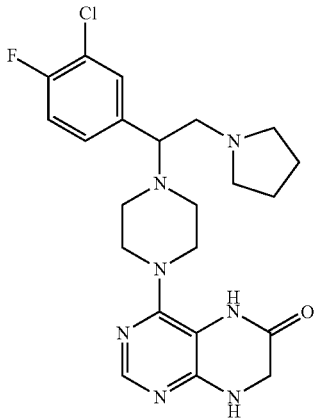 [SMILES: O=C1CNc2ncnc(N3CCN(C(CN4CCCC4)c4ccc(F)c(Cl)c4)CC3)c2N1]

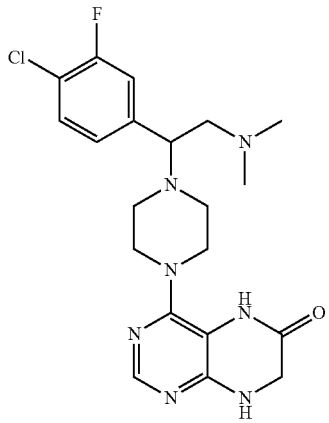

The title compound was prepared according to the procedure described for the preparation of A24, using 1-(2-chloro-2-(3-chloro-4-fluorophenyl)-ethyl)-pyrrolidine hydrochloride as the starting material. LC-MS: (M+1=460, obsd.=460);

$^1$H NMR (400 MHz, DMSO-d$_6$) δ [ppm]: 8.12 (s, 1H), 7.48-7.45 (m, 1H), 7.31-7.22 (m, 2H), 3.99 (s, 2H), 3.83 (s, 1H), 3.04 (q, J=6.9 Hz, 1H), 2.65-2.57 (m, 8H), 1.81 (s, 4H), 1.41 (s, 1H).

The title compound was prepared according to the procedure described for the preparation of A24, using 2-chloro-2-(4-chloro-3-fluorophenyl)-N,N-dimethylethanamine hydrochloride as the starting material. LC-MS: (M+1=432, obsd.=432);

$^1$H NMR (400 MHz, DMSO-d$_6$) δ [ppm]: 9.60 (s, 1H), 7.82 (s, 1H), 7.53 (d, J=6.8 Hz, 1H), 7.37 (d, J=10.3 Hz, 2H), 7.15 (d, J=7.2 Hz, 1H), 3.79 (s, 3H), 3.15 (s, 4H), 2.68 (s, 1H), 2.49 (s, 1H), 2.22 (s, 4H), 2.08 (s, 6H).

4-(4-(1-(3-chloro-4-fluorophenyl)-2-(pyrrolidin-1-yl)ethyl)piperazin-1-yl)-7,8-dihydropteridin-6(5H)-one "A57")

4-(4-(1-(4-chloro-3-fluorophenyl)-2-(methylamino)ethyl)piperazin-1-yl)-7,8-dihydropteridin-6(5H)-one ("A59")

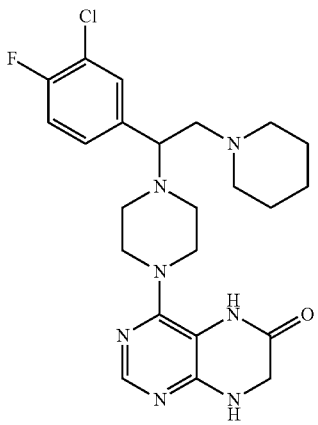 [SMILES: O=C1CNc2ncnc(N3CCN(C(CN4CCCCC4)c4ccc(F)c(Cl)c4)CC3)c2N1]

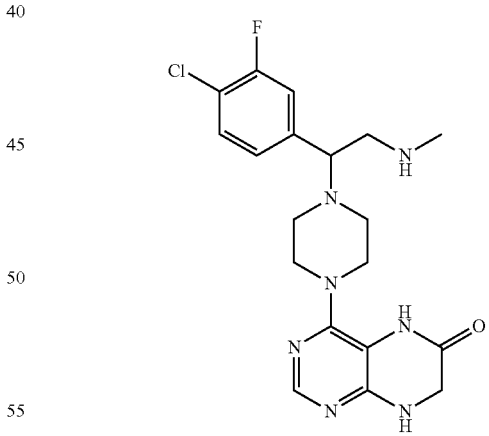

The title compound was prepared according to the procedure described for the preparation of A24, using 1-(2-chloro-2-(3-chloro-4-fluorophenyl)-ethyl)-piperidine hydrochloride as the starting material. LC-MS: (M+1=474, obsd.=474);

$^1$H NMR (400 MHz, DMSO-d$_6$) δ [ppm]: 9.59 (s, 1H), 7.81 (s, 1H), 7.50 (dd, J=1.5, 7.3 Hz, 1H), 7.38-7.27 (m, 3H), 3.76 (t, J=11.1 Hz, 3H), 3.15 (s, 4H), 2.72 (d, J=8.5 Hz, 1H), 2.66 (s, 1H), 2.50-2.48 (m, 5H), 2.40 (s, 2H), 1.36-1.32 (m, 6H), 1.23 (s, 1H).

The title compound was prepared according to the procedure described for the preparation of A24, using 2-chloro-2-(4-chloro-3-fluorophenyl)-N-methyl-ethanamine hydrochloride as the starting material. LC-MS: (M+1=420, obsd.=420);

$^1$H NMR (400 MHz, DMSO-d$_6$) δ [ppm]: 7.91 (d, J=3.1 Hz, 1H), 7.72 (d, J=8.1 Hz, 1H), 7.69-7.61 (m, 1H), 7.42-7.40 (m, 1H), 4.63 (s, 1H), 3.88 (s, 2H), 3.70 (s, 1H), 3.36 (s, 4H), 3.23 (s, 1H), 2.93 (s, 3H), 2.50-2.49 (m, 2H), 2.41 (s, 3H).

4-(4-(2-(azetidin-1-yl)-1-(4-chloro-3-fluorophenyl)
ethyl)piperazin-1-yl)-7,8-dihydropteridin-6(5H)-one
"A60")

4-(4-(1-(4-chloro-3-fluorophenyl)-2-(piperidin-1-yl)
ethyl)piperazin-1-yl)-7,8-dihydropteridin-6(5H)-one
("A62")

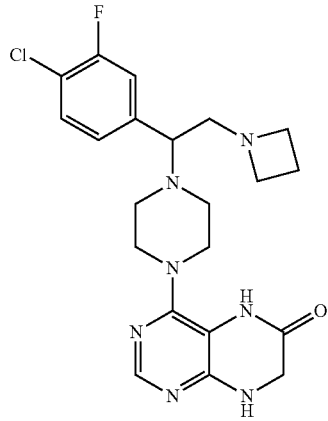 [SMILES: O=C1CNc2ncnc(N3CCN(C(CN4CCC4)c4ccc(Cl)c(F)c4)CC3)c2N1]

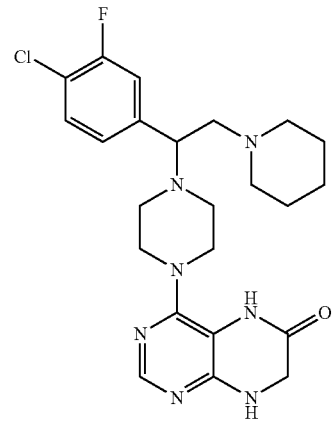

The title compound was prepared according to the procedure described for the preparation of A24, using 1-(2-chloro-2-(4-chloro-3-fluorophenyl)-ethyl)-azetidine hydrochloride as the starting material. LC-MS: (M+1=446, obsd.=446);

$^1$H NMR (400 MHz, DMSO-d$_6$) δ [ppm]: 8.28 (s, 2H), 7.80 (s, 1H), 7.49 (t, J=8.1 Hz, 1H), 7.30 (dd, J=1.7, 10.5 Hz, 1H), 7.17 (dd, J=1.4, 8.3 Hz, 1H), 3.80 (d, J=9.9 Hz, 2H), 3.60 (t, J=6.2 Hz, 1H), 3.22 (d, J=6.9 Hz, 2H), 3.19-3.07 (m, 6H), 2.49 (t, J=1.8 Hz, 3H), 2.41-2.29 (m, 3H), 1.97 (s, 2H).

The title compound was prepared according to the procedure described for the preparation of A24, using 1-(2-chloro-2-(4-chloro-3-fluorophenyl)-ethyl)-piperidine hydrochloride as the starting material. LC-MS: (M+1=474, obsd.=474);

$^1$H NMR (400 MHz, DMSO-d$_6$) δ [ppm]: 7.79 (s, 1H), 7.49 (t, J=8.0 Hz, 1H), 7.30 (dd, J=1.4, 10.7 Hz, 1H), 7.13 (d, J=8.2 Hz, 1H), 3.79 (s, 3H), 3.15 (s, 4H), 2.50-2.49 (m, 7H), 2.44 (s, 2H), 1.32 (d, J=21.6 Hz, 6H).

4-(4-(1-(4-chloro-3-fluorophenyl)-2-(pyrrolidin-1-yl)
ethyl)piperazin-1-yl)-7,8-dihydropteridin-6(5H)-one
("A61")

4-(4-(2((2-(dimethylamino)ethyl)amino)-1-(4-(trifluoromethyl)phenyl)-ethyl)piperazin-1-yl)-7,8-dihydropteridin-6(5H)-one ("A63")

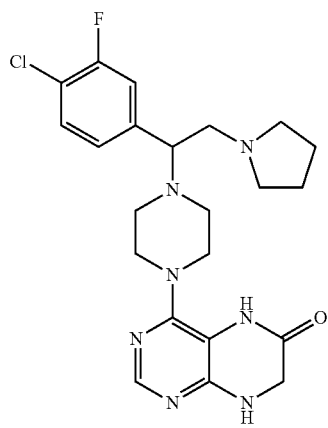 [SMILES: O=C1CNc2ncnc(N3CCN(C(CN4CCCC4)c4ccc(Cl)c(F)c4)CC3)c2N1]

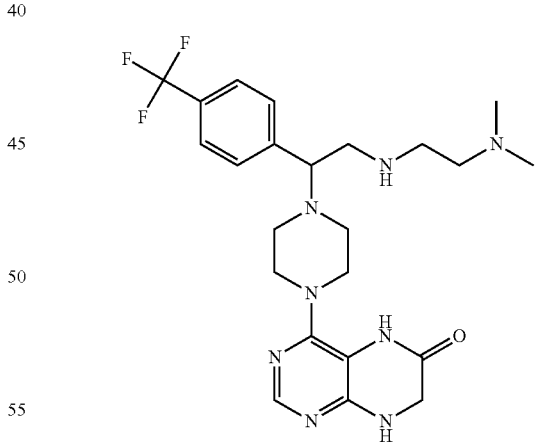

The title compound was prepared according to the procedure described for the preparation of A24, using 1-(2-chloro-2-(4-chloro-3-fluorophenyl)-ethyl)-pyrrolidine hydrochloride as the starting material. LC-MS: (M+1=460, obsd.=460);

$^1$H NMR (400 MHz, DMSO-d$_6$) δ [ppm]: 7.70 (s, 1H), 7.44 (t, J=8.0 Hz, 1H), 7.12 (dd, J=1.8, 10.1 Hz, 1H), 7.01 (t, J=8.2 Hz, 1H), 4.00-3.99 (m, 3H), 3.80 (t, J=12.6 Hz, 1H), 3.38 (dd, J=6.4, 13.0 Hz, 1H), 3.29 (s, 4H), 3.22 (s, 4H), 2.56-2.40 (m, 4H), 1.93 (s, 4H).

The title compound was prepared according to the procedure described for the preparation of A24, using N$^1$-(2-chloro-2-(4-(trifluoromethyl)phenyl)ethyl)-N$^2$,N$^2$-dimethylethane-1,2-diamine hydrochloride as the starting material. LC-MS: (M+1=493, obsd.=493);

$^1$H NMR (400 MHz, DMSO-d$_6$) δ [ppm]: δ 8.33 (s, 1H), 7.77 (s, 1H), 7.64 (d, J=8.1 Hz, 2H), 7.46 (d, J=8.0 Hz, 2H), 4.00-3.94 (m, 4H), 3.16 (s, 5H), 2.98-2.89 (m, 5H), 2.74-2.51 (m, 11H).

4-(4-(2-((2-(dimethylamino)ethyl)amino)-1-(3-(trifluoromethyl)phenyl)-ethyl)piperazin-1-yl)-7,8-dihydropteridin-6(5H)-one ("A64")

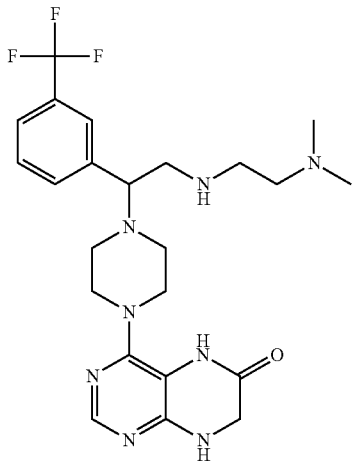 [SMILES: CN(C)CCNCC(c1cccc(C(F)(F)F)c1)N1CCN(c2ncnc3c2NC(=O)CN3)CC1]

The title compound was prepared according to the procedure described for the preparation of A24, using $N^1$-(2-chloro-2-(3-(trifluoromethyl)phenyl)ethyl)-$N^2$,$N^2$-dimethylethane-1,2-diamine hydrochloride as the starting material. LC-MS: (M+1=493, obsd.=493);

$^1$H NMR (400 MHz, DMSO-$d_6$) δ [ppm]: δ 9.63 (s, 1H), 8.19 (s, 1H), 7.86 (s, 1H), 7.73-7.61 (m, 2H), 7.59-7.53 (m, 2H), 7.31 (s, 1H), 3.94-3.90 (m, 1H), 3.83 (s, 2H), 3.23 (s, 4H), 2.67-2.63 (m, 2H), 2.54-2.41 (m, 6H), 2.39-2.28 (m, 8H).

4-(4-(2-((2-(dimethylamino)ethyl)amino)-1-(p-tolyl)ethyl)piperazin-1-yl)-7,8-dihydropteridin-6(5H)-one ("A65")

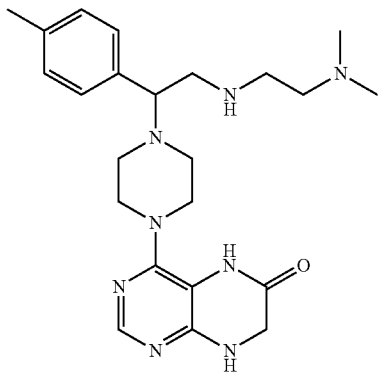

The title compound was prepared according to the procedure described for the preparation of A24, using $N^1$-(2-chloro-2-(p-tolyl)phenyl)-ethyl)-$N^2$,$N^2$-dimethylethane-1,2-diamine hydrochloride as the starting material. LC-MS: (M+1=439, obsd.=439);

$^1$H NMR (400 MHz, DMSO-$d_6$) δ [ppm]: δ 9.62 (s, 1H), 8.14 (s, 1H), 7.86 (s, 1H), 7.29 (t, J=8.4 Hz, 3H), 7.15 (d, J=7.9 Hz, 2H), 3.90 (s, 1H), 3.83 (s, 2H), 3.16 (s, 5H), 2.72 (s, 4H), 2.50-2.48 (m, 3H), 2.29 (d, J=6.56 Hz, 11H).

Biological Activity

The $IC_{50}$ values reported for the compounds in the Experimental section were derived from the following protocol for the p70S6K and AKT enzyme assays.

P70S6K Enzyme Assay

P70S6K inhibitor compounds were diluted and plated in 96 well plates. A reaction mixture including the following components was then added to the compound plate to initiate the enzyme reaction; P70S6K (3 nM, T412E mutant, Millipore) was mixed with 24 μM ATP in an assay buffer containing 100 mM Hepes (pH 7.5), 5 mM MgCl2, 1 mM DTT, 0.015% Brij and 1 μM of the substrate peptide FITC-AHA-AKRRRLSSLRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analysed on a Caliper Life Sciences Lab Chip 3000, using a pressure of −1.4 psi, and upstream and downstream voltages of −3000 and −700 respectively. Product peaks were resolved before substrate peaks on the resulting chromatograms.

The values for the p70S6K enzyme inhibition assay for selected compounds set out in the Experimental section are presented in Table 1 present functional data for selected compounds described by the present invention.

AKT Enzyme Assay

A TTP Mosquito liquid handling instrument was used to place 12.5 μl of the appropriate concentration of inhibitor in 100% DMSO (for a dose response curve calculation) into each well of a 384-well plate. To this reaction components were added to a final volume of 12.5 μl:

- 0.1 ng/μl His-AKT (Full Length), (Invitrogen, Part #P2999, Lot #641228C).
- 160 uM ATP (Fluka, 02055)
- 1 mM DTT (Sigma, D0632)
- 1 mM MgCl2 (Sigma, M1028)
- 1 μM substrate peptide (sequence FITC-AHA-GRPRTSS-FAEG-NH2), synthesized by Tufts Peptide Synthesis service.
- 100 mM HEPES pH 7.5 (Calbiochem, 391338)
- 0.015% Brij-35 (Sigma, B4184)

The reaction was incubated for 90 min at 25° C., and then stopped by the addition of 70 μl of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure −2.3 psi, upstream voltage −500, and downstream voltage −3000. These conditions caused unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an IC50 was calculated.

The values for the p70S6K and AKT enzyme inhibition assays for selected compounds set out in the Experimental section are presented in Table 1. The data are presented as follows:

+++++: <25 nM;
++++: 25-100 nM;
+++: 101 nM-500 nM;
++: 501 nM-1000 nM;
+: >1 μM.

TABLE 1 p70S6K Enzyme Inhibition by Compounds Described by Formula (I)

| Compound No. | IC$_{50}$ p70S6K (nM) | IC$_{50}$ AKT (nM) |
|---|---|---|
| A1 | ++++ | +++ |
| A2 | ++++ | ++++ |
| A3 | + | + |
| A4 | + | +++ |
| A5 | + | +++ |
| A6 | +++ | +++ |
| A7 | +++ | +++ |
| A8 | +++ | ++++ |
| A9 | ++++ | ++++ |
| A10 | ++ | +++ |
| A11 | ++ | +++ |
| A12 | ++ | +++ |
| A13 | ++++ | +++ |
| A14 | ++ | ++ |
| A15 | +++ | +++ |
| A16 | ++++ | ++++ |
| A17 | +++ | ++++ |
| A18 | +++ | ++++ |
| A19 | ++++ | ++++ |
| A20 | +++ | ++++ |
| A21 | + | ++ |
| A22 | +++ | ++++ |
| A23 | + | + |
| A24 | + | + |
| A25 | + | + |
| A26 | ++ | +++ |
| A27 | + | + |
| A28 | ++ | +++ |
| A29 | + | + |
| A30 | ++ | ++ |
| A31 | + | + |
| A32 | + | ++ |
| A33 | + | ++ |
| A34 | + | + |
| A35 | + | + |
| A36 | + | + |
| A37 | + | + |
| A38 | + | + |
| A39 | + | + |
| A40 | + | + |
| A41 | + | + |
| A42 | + | + |
| A43 | + | + |
| A44 | + | + |
| A45 | + | + |
| A46 | + | + |
| A47 | + | + |
| A48 | + | + |
| A49 | + | + |
| A50 | + | + |
| A51 | + | + |
| A52 | + | + |
| A53 | + | + |
| A54 | + | + |
| A55 | + | + |
| A56 | + | + |
| A57 | + | + |
| A58 | + | +++ |
| A59 | + | + |
| A60 | + | + |
| A61 | + | +++ |
| A62 | + | ++ |
| A63 | + | + |
| A64 | + | + |
| A65 | + | + |

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

We claim:
1. A compound of formula (I),

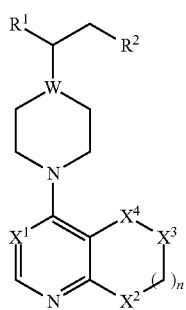

or a pharmaceutically acceptable salt, solvate, solvate of salts, tautomer or stereoisomer, including a mixture thereof in all ratios thereof,
wherein:
$X^1$ is N,
$X^2$ is $CH_2$ or NH,
$X^3$ is $CH_2$,
$X^4$ is O, $CH_2$ or NH,
W is N or CH,
$R^1$ is Ar or Het,
$R^2$ is $[C(R^3)_2]_p Het^1$ or $[C(R^3)_2]_p N(R^3)_2$,
each $R^3$ is independently H or alkyl with 1, 2, 3, or 4 C-atoms, which is optionally substituted;
Ar is phenyl which is unsubstituted or mono-, di- or trisubstituted by Hal, A, phenyl, $CON(R^3)_2$, $COOR^3$, $NHCOA$, $NHSO_2A$, CHO, COA, $SO_2N(R^3)_2$, $SO_2A$, $[C(R^3)_2]_p OR^3$, $[C(R^3)_2]_p N(R^3)_2$ and/or $[C(R^3)_2]_p CN$,
Het is furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, pyrazinyl, indolyl, isoindolyl, benzimidazolyl, indazolyl or quinolyl, which is unsubstituted or mono-, di- or trisubstituted by Hal, A, $[C(R^3)_2]_p OR^3$, $[C(R^3)_2]_p N(R^3)_2$, $NO_2$, CN, $[C(R^3)_2]_p COOR^3$, $CON(R^3)_2$, $NR^3 COA$, $NR^3 SO_2A$, $SO_2N(R^3)_2$, $S(O)_m A$ and/or $O[C(R^3)_2]_q N(R^3)_2$,
$Het^1$ is dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, azepanyl, morpholinyl, hexahydropyridazinyl, hexahydropyrimidinyl, [1,3]dioxolanyl, tetrahydropyranyl, pyridyl or piperazinyl, which is unsubstituted or mono- or disubstituted by A,
each A is independently unbranched or branched alkyl with 1-10 C-atoms, wherein one or two non-adjacent CH- and/or $CH_2$-groups may be replaced by N-, O- and/or S-atoms and wherein 1-7 H-atoms may be replaced by F or Cl,
each Hal is independently F, Cl, Br or I,
each m is independently 0, 1 or 2,
each n is independently 0, 1 or 2,
each p is independently 0, 1, 2, 3 or 4,
each q is independently 2, 3 or 4.

2. The compound according to claim 1, or a pharmaceutically acceptable salt, solvate, solvate of salts, tautomer or stereoisomer, including a mixture thereof in all ratios thereof,
wherein:
$X^1$ is N,
$X^2$ is $CH_2$ or NH,
$X^3$ is $CH_2$,
$X^4$ is $CH_2$ or NH,
W is N or CH,
$R^1$ is Ar,
$R^2$ is $[C(R^3)_2]_p Het^1$ or $[C(R^3)_2]_p N(R^3)_2$,
each $R^3$ is independently H or methyl,
Ar is phenyl which is unsubstituted or mono- or disubstituted by Hal and/or A,
$Het^1$ is pyrrolidinyl, azetidinyl or piperidinyl,
each A is independently unbranched or branched alkyl with 1-10 C-atoms, wherein one or two non-adjacent CH- and/or $CH_2$-groups may be replaced by N- and/or O-atoms and wherein 1-7 H-atoms may be replaced by F or Cl, or Cyc,
Cyc is cyclic alkyl with 3-7 C-atoms,
Hal is F, Cl, Br or I,
each n is independently 0 or 1,
each p is independently 0, 1, 2, 3 or 4.

3. The compound according to claim 1, or a pharmaceutically acceptable salt, solvate, solvate of salts, tautomer or stereoisomer, including a mixture thereof in all ratios thereof, selected from the group:
2-(1-(5,6,7,8-tetrahydro-1,8-naphthyridin-4-yl)piperidin-4-yl)-2-(4-(trifluoromethyl)phenyl)ethanamine ("A1")
2-(1-(2,3-dihydro-1H-pyrrolo[2,3-b]pyridin-4-yl)piperidin-4-yl)-2-(4-(trifluoro-methyl)phenyl)ethanamine ("A2")
2-(1-(6,7-dihydro-5H-cyclopenta[b]pyridin-4-yl)piperidin-4-yl)-2-(4-(trifluoromethyl)phenyl)ethanamine ("A3")
{2-(4-Chlorophenyl)-2-[4-(7,8-dihydro-6H-pyrimido[5,4-b][1,4]oxazin-4-yl)-piperazin-1-yl]-ethyl}-dimethylamine ("A4")
[2-[4-(7,8-Dihydro-6H-pyrimido[5,4-b][1,4]oxazin-4-yl)-piperazin-1-yl]-2-(4-trifluoromethylphenyl)-ethyl]-dimethylamine ("A5")
[2-[4-(6,7-Dihydro-5H-pyrrolo[2,3-d]pyrimidin-4-yl)-piperazin-1-yl]-2-(4-trifluoromethylphenyl)-ethyl]-dimethylamine ("A6")
{2-(4-Chlorophenyl)-2-[4-(6,7-dihydro-5H-pyrrolo[2,3-d]pyrimidin-4-yl)-piperazin-1-yl]-ethyl}-dimethylamine ("A7")
{2-(4-Chlorophenyl)-2-[4-(5,6,7,8-tetrahydro-pyrdio[2,3-d]pyrimidin-4-yl)-piperazin-1-yl]-ethyl}-dimethylamine ("A8")
Dimethyl-[2-[4-(5,6,7,8-tetrahydro-pyrido[2,3-d]pyrimidin-4-yl)-piperazin-1-yl]-2-(4-trifluoromethyl-phenyl)-ethyl]-amine ("A9")
2-[4-(7,8-Dihydro-6H-pyrimido[5,4-b][1,4]oxazin-4-yl)-piperazin-1-yl]-2-(4-trifluoromethylphenyl)-ethylamine ("A10")
2-(4-Chlorophenyl)-2-[4-(7,8-dihydro-6H-pyrimido[5,4-b][1,4]oxazin-4-yl)-piperazin-1-yl]-ethylamine ("A11")
[2-[4-(7,8-Dihydro-6H-pyrimido[5,4-b][1,4]oxazin-4-yl)-piperazin-1-yl]-2-(3-fluoro-4-trifluoromethylphenyl)-ethyl]-dimethylamine ("A12")

2-(4-Chloro-phenyl)-2-[4-(6,7-dihydro-5H-pyrrolo[2,3-d]pyrimidin-4-yl)-piperazin-1-yl]-ethylamine ("A13")
2-[4-(6,7-Dihydro-5H-pyrrolo[2,3-d]pyrimidin-4-yl)-piperazin-1-yl]-2-(4-fluorophenyl)-ethylamine ("A14")
{2-(4-Chloro-3-fluoro-phenyl)-2-[4-(6,7-dihydro-5H-pyrrolo[2,3-d]pyrimidin-4-yl)-piperazin-1-yl-ethyl}-dimethylamine ("A15")
2-[4-(5,6,7,8-Tetrahydro-pyrdio[2,3-d]pyrimidin-4-yl)-piperazin-1-yl]-2-(4-trifluoromethyl-phenyl)-ethylamine ("A16")
2-(4-Chloro-phenyl)-2-[4-(5,6,7,8-tetrahydro-pyrido[2,3-d]pyrimidin-4-yl)-piperazin-1-yl]-ethylamine ("A17")
{2-(4-Chloro-3-fluoro-phenyl)-2-[4-(5,6,7,8-tetrahydro-pyrido[2,3-d]pyrimidin-4-yl)-piperazin-1-yl]-ethyl}-dimethylamine ("A18")
{2-(3-Fluoro-4-trifluoromethyl-phenyl)-2-[4-(5,6,7,8-tetrahydro-pyrdio[2,3-d]pyrimidin-4-yl)-piperazin-1-yl]-ethyl}-dimethylamine ("A19")
2-(4-fluorophenyl)-2-[4-(7,8-dihydro-6H-pyrimido[5,4-b][1,4]oxazin-4-yl)-piperazin-1-yl]-ethylamine ("A20")
[2-[4-(6,7-Dihydro-5H-pyrrolo[2,3-d]pyrimidin-4-yl)-piperazin-1-yl]-2-(3-fluoro-4-trifluoromethyl-phenyl)-ethyl]-dimethylamine ("A21")
2-(4-Fluoro-phenyl)-2-[4-(5,6,7,8-tetrahydro-pyrido[2,3-d]pyrimidin-4-yl)-piperazin-1-yl]-ethylamine ("A22") and
2-[1-(7,8-Dihydro-6H-pyrimido[5,4-b][1,4]oxazin-4-yl)-piperidin-4-yl]-2-(4-trifluoromethyl-phenyl)-ethylamine ("A23").

4. The compound of claim 1, wherein $R^3$ is H or methyl.

5. The compound of claim 1, wherein Ar is phenyl which is unsubstituted or mono- or disubstituted by Hal and/or A.

6. The compound of claim 1, wherein Het is pyridyl or pyrimidyl, which is unsubstituted or monosubstituted by A.

7. The compound of claim 1, wherein $Het^1$ is pyrrolidinyl, azetidinyl or piperidinyl.

8. The compound of claim 1, wherein $R^1$ is

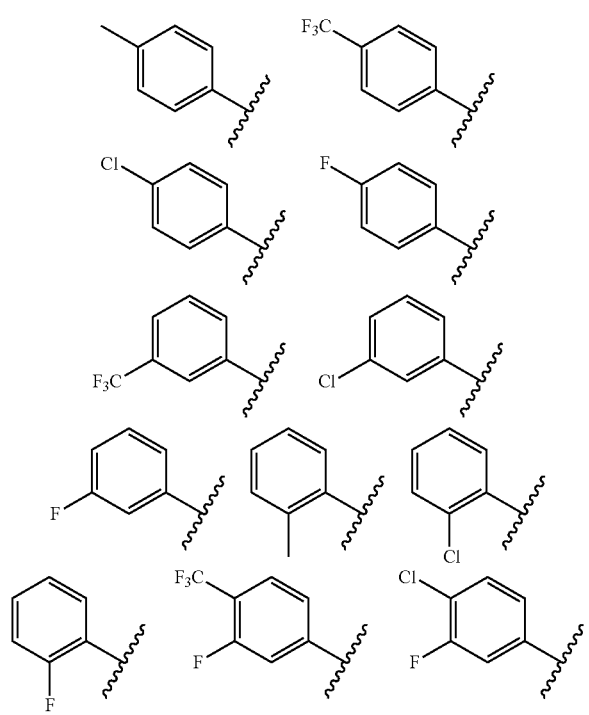

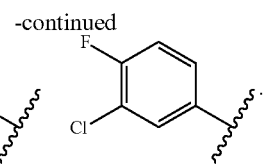

9. The compound of claim 1, wherein $R^2$ is

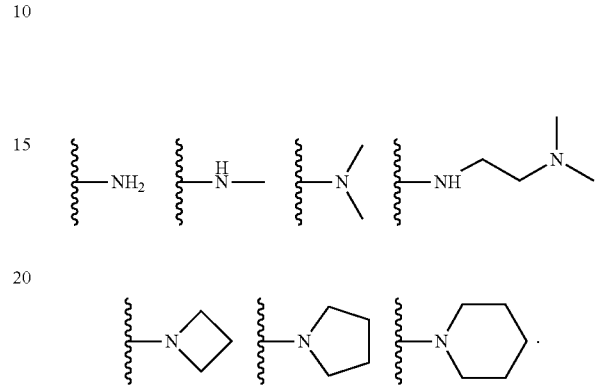

10. The compound of claim 1, of formula I-f:

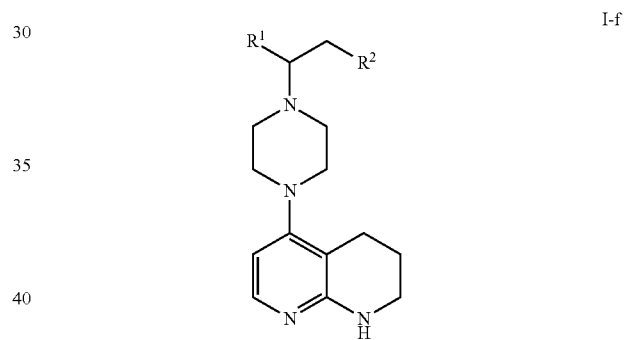

or a pharmaceutically acceptable salt, solvate, solvate of salts, tautomer or stereoisomer, including a mixture thereof in all ratios thereof.

11. The compound of claim 1, of formula I-g:

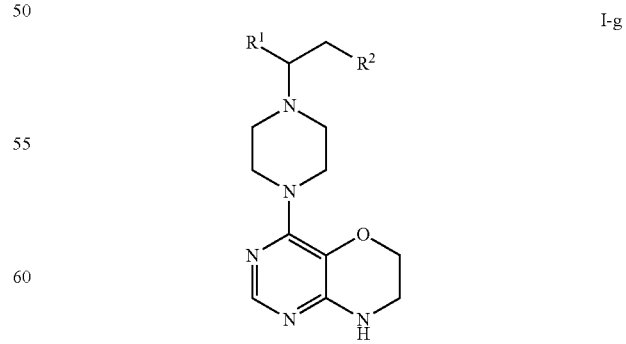

or a pharmaceutically acceptable salt, solvate, solvate of salts, tautomer or stereoisomer, including a mixture thereof in all ratios thereof.

12. The compound of claim 1, of formula I-i:

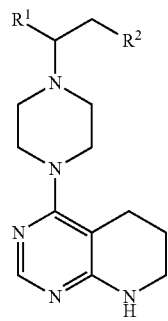

I-i or a pharmaceutically acceptable salt, solvate, solvate of salts, tautomer or stereoisomer, including a mixture thereof in all ratios thereof.

13. A pharmaceutical composition comprising at least one compound of claim 1 or a pharmaceutically acceptable salt, solvate, solvate of salts, tautomer or stereoisomer, including a mixture thereof in all ratios thereof, and optionally an pharmaceutically acceptable carrier, excipient or vehicle.

14. A process for the preparation of compounds of claim 1 and pharmaceutically acceptable salts, solvates, solvates of salts, tautomers or stereoisomers, including mixtures thereof in all ratios thereof, comprising:

a) reacting a compound of formula (II)

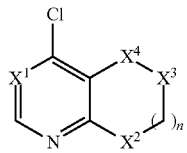

(II)

wherein
$X^1$ is N or CH,
$X^2$ is $CH_2$ or NH,
$X^3$ is $CH_2$ or CO,
$X^4$ is O, $CH_2$ or NH,
with a compound of formula (III)

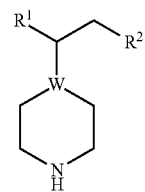

(III)

wherein
W is N or CH,
$R^1$ is Ar or Het,
$R^2$ is $[C(R^3)_2]_p Het^1$ or $[C(R^3)_2]_p N(R^3)_2$,
or
b) for the preparation of a compound of claim 1, wherein $X^3$ is CO and $X^4$ is NH,
a compound of formula (IV)

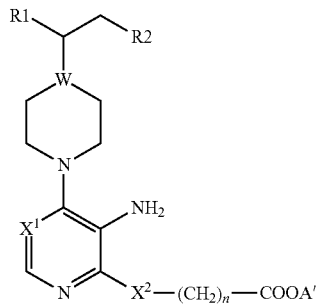

(IV)

wherein
$X^1$ is N or CH,
$X^2$ is $CH_2$ or NH,
$X^3$ is $CH_2$ or CO,
$X^4$ is O, $CH_2$ or NH,
W is N or CH,
$R^1$ is Ar or Het,
$R^2$ is $[C(R^3)_2]_p Het^1$ or $[C(R^3)_2]N(R^3)_2$, and
A' is alkyl with 1, 2, 3 or 4 C-atoms,
is cyclised,
and/or
a base or acid of the compound of claim 1 is converted into one of its salts.

* * * * *